United States Patent [19]

Mathes et al.

[11] 4,307,152

[45] Dec. 22, 1981

[54] HYDROPHILIC POLYESTER FIBER AND PROCESS FOR MAKING SAME

[75] Inventors: Nikolaus Mathes, Breuberg; Wolfgang Lange, Obernburg; Klaus Gerlach, Aschaffenburg, all of Fed. Rep. of Germany

[73] Assignee: Akzona Incorporated, Asheville, N.C.

[21] Appl. No.: 68,880

[22] Filed: Aug. 22, 1979

Related U.S. Application Data

[63] Continuation-in-part of Ser. No. 968,775, Dec. 12, 1978, abandoned.

[30] Foreign Application Priority Data

Dec. 12, 1977 [DE] Fed. Rep. of Germany ....... 2755341

[51] Int. Cl.$^3$ .............................................. D02G 3/00
[52] U.S. Cl. ...................... 428/373; 264/41; 264/171; 264/177 F; 264/211; 428/376; 428/398
[58] Field of Search ............... 428/398, 373, 374, 376; 528/274, 282; 260/45.75 R, 45.85 R; 264/41, 171, 177 F, 211

[56] References Cited

U.S. PATENT DOCUMENTS

| | | |
|---|---|---|
| 1,225,414 | 5/1917 | Craig . |
| 2,711,402 | 6/1955 | Fletcher . |
| 2,780,571 | 2/1957 | Downing et al. . |
| 2,850,483 | 9/1958 | Ballentine et al. . |
| 2,960,490 | 11/1960 | Hinkes . |
| 2,987,373 | 6/1961 | Bezemer et al. . |
| 3,100,675 | 8/1963 | Westerhuis et al. . |
| 3,163,492 | 12/1964 | Thomas . |
| 3,164,567 | 1/1965 | Horn . |
| 3,166,531 | 1/1965 | Horn . |
| 3,264,255 | 8/1966 | Taylor . |
| 3,303,045 | 2/1967 | Newman ........................ 428/280 X |
| 3,313,768 | 4/1967 | Veazey et al. . |
| 3,318,856 | 5/1967 | Deyrup . |
| 3,342,898 | 9/1967 | Roselli . |
| 3,357,944 | 12/1967 | Dexter et al. . |
| 3,374,200 | 3/1968 | Deichert . |
| 3,382,209 | 5/1968 | Deichert . |
| 3,423,491 | 1/1969 | McLain et al. ........................ 264/49 |
| 3,475,371 | 10/1969 | Stewart et al. . |
| 3,488,318 | 1/1970 | Stewart et al. . |
| 3,513,110 | 5/1970 | Noether ........................ 264/346 X |
| 3,516,239 | 6/1970 | Fukuda et al. ........................ 428/373 |
| 3,637,542 | 1/1972 | Doerge et al. . |
| 3,647,724 | 3/1972 | Doerge et al. . |
| 3,652,493 | 3/1972 | Stewart . |
| 3,682,846 | 8/1972 | Sano et al. ........................ 260/860 X |
| 3,720,744 | 3/1973 | Santangelo ........................ 264/205 |
| 3,748,844 | 7/1973 | Pacofsky . |
| 3,821,163 | 6/1974 | Spivack . |
| 3,833,542 | 9/1974 | Lazarus et al. . |
| 3,872,052 | 3/1975 | Fielding et al. . |
| 3,878,166 | 4/1975 | Woycheshin et al. . |
| 3,926,551 | 12/1975 | Okada et al. ........................ 8/115.6 X |
| 3,953,405 | 4/1976 | Feinauer et al. . |
| 3,956,538 | 5/1976 | Vartiak . |
| 3,957,936 | 5/1976 | Lauchenauer ........................ 428/398 X |
| 3,965,068 | 6/1976 | Dickens, Jr. . |
| 3,969,462 | 7/1976 | Stofan . |
| 3,975,356 | 8/1976 | Dickens, Jr. . |
| 4,000,109 | 12/1976 | Smith et al. . |
| 4,001,367 | 1/1977 | Guthrie et al. ........................ 264/154 |
| 4,043,985 | 8/1977 | Vock . |
| 4,070,342 | 1/1978 | Lazarus et al. . |
| 4,101,525 | 7/1978 | Davis et al. . |
| 4,116,931 | 9/1978 | Minhas et al. . |
| 4,134,882 | 1/1979 | Frankfort et al. . |
| 4,163,078 | 7/1979 | Reinehr et al. ........................ 428/373 |
| 4,164,603 | 8/1979 | Siggel et al. ........................ 264/211 X |
| 4,169,827 | 10/1979 | Gerlach et al. .............. 260/45.75 R |

FOREIGN PATENT DOCUMENTS

| | | |
|---|---|---|
| 695184 | 8/1967 | Belgium . |
| 848592 | 5/1977 | Belgium . |
| 1941189 | 3/1971 | Fed. Rep. of Germany . |
| 2526749 | 10/1976 | Fed. Rep. of Germany . |
| 2550081 | 4/1977 | Fed. Rep. of Germany ...... 264/171 |
| 2552511 | 6/1977 | Fed. Rep. of Germany . |
| 2554124 | 6/1977 | Fed. Rep. of Germany . |
| 2607071 | 8/1977 | Fed. Rep. of Germany . |
| 2703372 | 8/1977 | Fed. Rep. of Germany . |
| 2607059 | 9/1977 | Fed. Rep. of Germany . |
| 2607996 | 9/1977 | Fed. Rep. of Germany . |
| 2609829 | 9/1977 | Fed. Rep. of Germany . |
| 2610626 | 9/1977 | Fed. Rep. of Germany . |
| 2611193 | 9/1977 | Fed. Rep. of Germany . |
| 2709403 | 9/1977 | Fed. Rep. of Germany . |

| | | |
|---|---|---|
| 2625908 | 12/1977 | Fed. Rep. of Germany . |
| 2627708 | 12/1977 | Fed. Rep. of Germany . |
| 2628964 | 12/1977 | Fed. Rep. of Germany . |
| 2628902 | 1/1978 | Fed. Rep. of Germany . |
| 2633838 | 2/1978 | Fed. Rep. of Germany . |
| 2637394 | 2/1978 | Fed. Rep. of Germany . |
| 2642195 | 3/1978 | Fed. Rep. of Germany . |
| 2657144 | 6/1978 | Fed. Rep. of Germany . |
| 2757787 | 6/1978 | Fed. Rep. of Germany . |
| 2659263 | 7/1978 | Fed. Rep. of Germany . |
| 2659616 | 7/1978 | Fed. Rep. of Germany . |
| 2703051 | 7/1978 | Fed. Rep. of Germany . |
| 2705210 | 8/1978 | Fed. Rep. of Germany . |
| 2706032 | 8/1978 | Fed. Rep. of Germany . |
| 2706522 | 8/1978 | Fed. Rep. of Germany . |
| 2713456 | 9/1978 | Fed. Rep. of Germany . |
| 2044281 | 10/1978 | Fed. Rep. of Germany . |
| 2719019 | 11/1978 | Fed. Rep. of Germany . |
| 2724952 | 12/1978 | Fed. Rep. of Germany . |
| 2736065 | 2/1979 | Fed. Rep. of Germany . |
| 2737404 | 2/1979 | Fed. Rep. of Germany . |
| 2739179 | 4/1979 | Fed. Rep. of Germany . |
| 7410205 | 3/1974 | France . |
| 48-27608 | 8/1973 | Japan ................................ 264/177 F |
| 53022171 | 8/1976 | Japan . |
| 1130065 | 10/1968 | United Kingdom . |
| 1195098 | 6/1970 | United Kingdom . |
| 1292388 | 10/1972 | United Kingdom . |
| 1304086 | 1/1973 | United Kingdom . |
| 1379752 | 1/1975 | United Kingdom . |
| 1541942 | 3/1979 | United Kingdom . |
| 1543423 | 4/1979 | United Kingdom . |
| 1558308 | 12/1979 | United Kingdom . |

OTHER PUBLICATIONS

Chemical Abstracts 52, 12198d (1964).
Penisson, R., "Wege zur Modifizierung von Chemifasern", Lenzinger Berichte 36, pp. 24 to 34, (Feb. 1974).
Wikerei-und Strickerei-Technik, Coburg No. 9, pp. 442 to 445, (Sep. 1977).
Kleber, R., Lenzinger Berichte 33, pp. 64 to 71, (Dec. 1972).
Geleji, F. et al., Lenzinger Berichte 33, pp. 199 to 207, (Dec. 1972).
Sharma, V. N., "Hydrophilicity of Textile Fibers and Its Influence on Fabric Wear Properties", Colourage, 23 to 27 (May 11, 1978).
Teichmann, R., Fasernforschung und Textiltechnik 26(2), pp. 66 to 88, (1975).
Hochman, V., Fasernforschung und Textiltechnik 27, pp. 417 to 424 (1976).
Statton, W. O., Journal of Polymer Science, vol. XLI, pp. 143 to 155 (1959).
Statton, W. O., Journal of Polymer Science, vol. XXII, pp. 385 to 397 (1956).
Sarmany, C. et al., Lenzinger Berichte 44, pp. 85 to 89 (Jan. 1978).
Hoigne, J. et al., Textileveredlung 5(5), pp. 400 to 406 (1970).
Peitscher, M. et al., Textil Praxis International, pp. 1180 to 1190 (Oct. 1976).
Robinson, T., Textilveredlung 12(6), pp. 264 to 268 (1977).
Statton, W. O., Journal of Polymer Science, vol. 58, pp. 205 to 220 (1962).
Dolmetsch, H., Chemiefasern/Textil-industrie, pp. 1086 to 1095 (Dec. 1976).
Weigmann, H. D., et al., Melliand Textilberichte, pp. 470 to 473 (Jun. 1976).
Krishnamurty, K. V. et al., "The Chemistry of Metal Oxalato Complexes", Chemical Reviews 67, pp. 213 to 246 (1961).
Hoffmann, P., Teintex, No. 4, pp. 174 to 186, 1977.
Donze, J.-J. et al., Bull. Scient. ITF, vol. 4, No. 14, pp. 129 to 138 (May 1975).
Chegolya, A. S., Fibre Chemistry, vol. 9, No. 6, pp. 522 to 530 (Nov.-Dec. 1977).
Weigmann, H. D. et al., Textile Research Journal, 46, pp. 574 to 587 (Aug. 1976).
Weigmann, H. D. et al., Journ. of App. Polymer Science, vol. 20, pp. 2321 to 2327 (1976).
Seghezzi, H., Wirkerei-und Strickerei-Technik, Bamberg, No. 12, pp. 705 to 708 (Dec. 1978).
Umbach, K.-H., Chemiefasern/Textilindustrie, pp. 42 to 47 (Jan. 1979).
Weigmann, H.-D., et al., Progress Report No. 26, Apr. 1, 1976-Jul. 31, 1976, Textile Reserach Institute, Aug. 16, 1976.
Ribnick, A. S. et al., Textile Research Journal, vol. 43, pp. 176 to 183 (Mar. 1973).
Rebenfeld, L., Lenzinger Berichte 40, pp. 22 to 29 (May 1976).
Sotton, M. et al., Bull. Sci. Inst. Textiles France, 24(150), pp. 763 to 781 (1970).

Weigmann, H.-D., et al., Textile Research Journal, pp. 165 to 173 (Mar. 1974).
Knox, B. H. et al., Textile Reserach Journal, pp. 203 to 217 (Mar. 1975).
Weigmann, H.-D., et al., Progress Report No. 27, Aug. 1, 1976–Nov. 30, 1976, Textile Research Institute, Jan. 20, 1977.

*Primary Examiner*—Lorraine T. Kendell
*Attorney, Agent, or Firm*—Robert H. Falk; Charles A. Wendel; Francis W. Young

[57] ABSTRACT

A new and useful hydrophilic polyester fiber and process of making same are disclosed; the fiber has a stable pore system exhibiting a moisture pickup (regain) of at least about 2 percent by weight at 40° C. and a relative humidity of 92%. Our experiments indicate that the proportion of moisture regain is attributable to capillary condensation in an amount of at least 25%. The hydrophilic properties are the result of a certain pore system within the fiber which enables capilliary condensation to occur significantly. The invention describes one way to accomplish this, namely by the addition of a predetermined amount of a suitable oxalato-complex to a suitable polyester mass. Most preferably, about 10% by weight $K_3Al(C_2O_4)_3$ is added to the polyester mass. The fibers are produced by extruding a suitable polyester mass containing 1 to 20 percent by weight of a suitable oxalato complex to form a filament, drawing the filament, and hydrosetting the drawn filament at a suitable temperature, generally between about 90° C. and about 170° C., preferably between about 120° C. and about 140° C., under pressure, and in the presence of liquid water.

The hydrophilic polyester produced by the novel process has the favorable moisture regain and many of the favorable texture qualities of cotton, together with the quick drying qualities of conventional polyester fiber.

18 Claims, 8 Drawing Figures

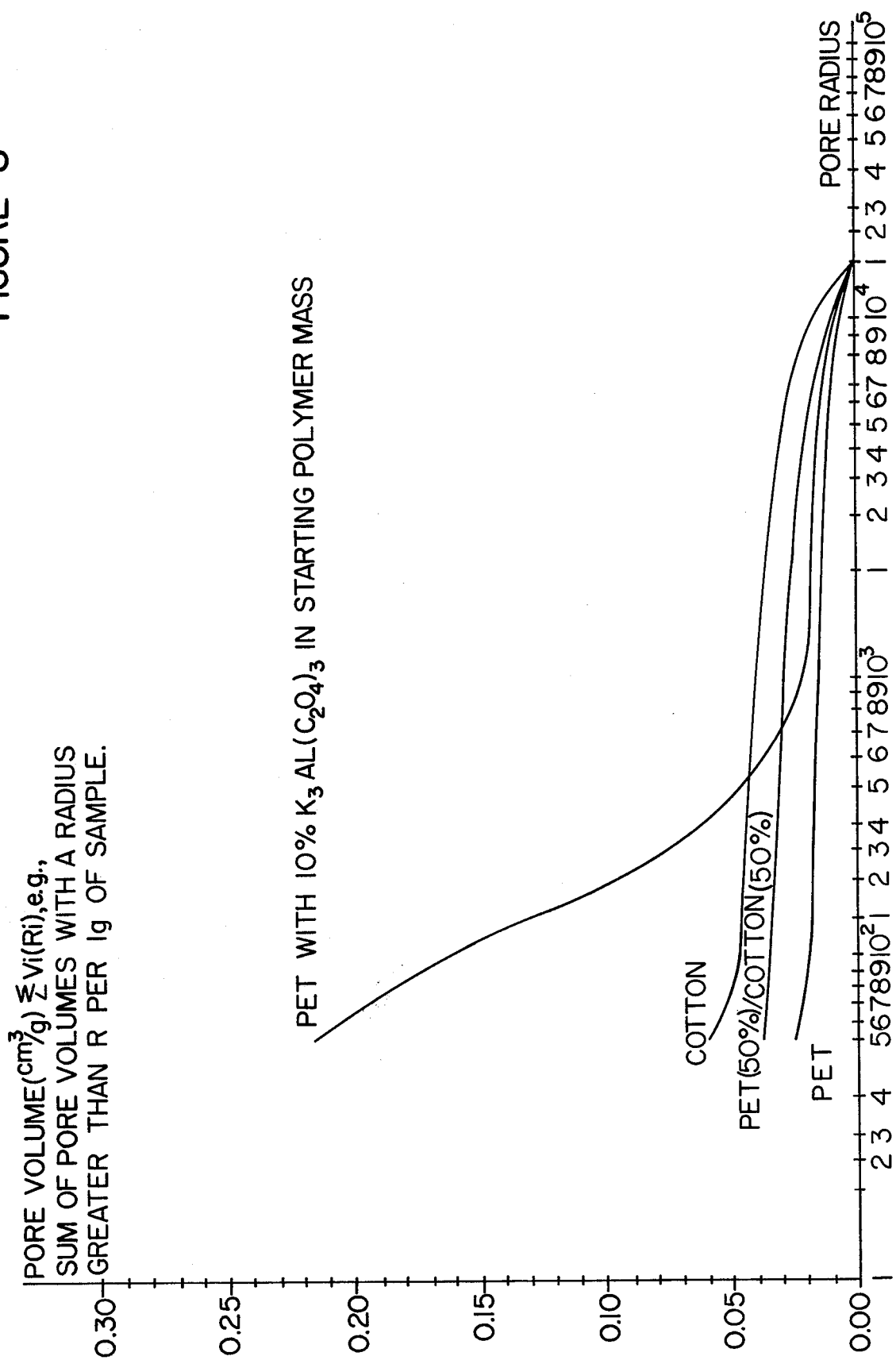

HYDROPHILIC POLYESTER FIBER AND PROCESS FOR MAKING SAME

RELATED CASES

This application is a continuation-in-part of Ser. No. 968,775, filed Dec. 12, 1978 now abandoned in favor of the instant application, for which priority is claimed under 35 U.S.C. S119 to Ger. Pat. Off. 27,55,341.9.

This application is related by subject matter to application Ser. No. 774,073, filed Mar. 3, 1977, "Flame Resistant and Self-Extinguishing Polymers", issued as U.S. Pat. No. 4,169,827 on Oct. 2, 1979, by Klaus Gerlach and Wolfgang Lange, which is incorporated herein.

BACKGROUND OF THE INVENTION

1. Field of the Invention

The invention pertains to synthetic textiles, and particularly to textiles made of hydrophilic polyesters.

2. Description of the Prior Art, and Other Information

The wearing hygiene and, consequently, wearing comfort of a textile depends essentially on the ability of the textile to transport heat and moisture. Natural fibers, such as cotton and wool, are hydrophilic, i.e., they absorb considerable amounts of atmospheric moisture and also exhibit a high absorbency and a high water retention capacity.[1] When compared with polyester fibers, natural fibers have certain drawbacks, especially when the person wearing a natural fiber textile tends to release much heat and starts to perspire. For instance, during swelling, the fiber cross section of wool increases by about 25% and that of polyester by only about 1%. Robinson, Textilpraxis International at 1180 (1976). This inhibits the permeability of the fiber to air and thus the direct transport of moisture through the meshes of the textile, especially with dense textiles. Moreover, the absorption (here absorption shall refer also to adsorption) of water by wool produces far more additional heat (113 J/g water or 27 cal/g water) than the absorption of water by polyester (3.35 J/g water or 0.8 cal/g water). Robinson, Textilveredlung at 264 (1977). Closely relates to this heat effect is the fact that with increasing temperature the absorption capacity of wool declines distinctly.[2] Finally, polyester textiles dry much faster than wool textiles. The advantage of polyester in this respect is derived in particular from the fact that it absorbs much less water than wool. On the other hand, the low water absorbency (quality of having a relative tendency to absorb) of polyester is at least partly responsible for the unsatisfactory wearing hygiene and low wearing comfort of polyester fiber, together with polyester's relatively poor "feel" to the wearer, e.g., "hand". The objective of some in the art in the past five to ten years has been to try to improve this significant drawback, i.e., in particular, to increase the moisture pickup (or regain) and the water retention capacity, which are the decisive criteria of a hydrophilic behavior (cf., Robinson supra), without sacrificing favorable polyester properties.[3]

[1] Hydrophilicity is the tendency of a material to exhibit a strong affinity for water, or to be readily wetted by water.
[2] Absorption capacity is the maximum amount of moisture which a specimen may absorb under a given set of conditions.
[3] Moisture pickup or moisture regain is the percentage of moisture in a textile material brought into equilibrium with a standard atmosphere, calculated as a percentage of the moisture-free weight.

There exists a large number of porous polyester fibers obtained by special drawing methods or by foaming with an inert gas. Like dry spun hydrophilic polyacrylonitrile fibers, the porous polyester fibers contain large pores recognizable under the light microscope which, however, do not significantly increase the moisture regain.

Porous polyester fibers with fine capillary pores not detectable under the light microscope are known to those in the art. To improve the dye rate and the relative dye uptake, H. D. Weigmann, et al., (Melliand Textilberichte at 470–473 (1976/6) have treated polyester fibers with dimethyl formamide, with subsequent treatment in boiling water to remove the solvent, followed by drying and a thermal treatment.[4] The Weigmann, et al., treatment led to structural changes which are essentially the result of disorientation processes in the noncrystalline regions. Depending on the temperature of the solvent treatment, a more or less pronounced secondary crystallization takes place, induced by the interaction between polymers and solvents, leading to the formation of crystallites in the swollen fiber structure. Stabilization of the swollen fiber structure prevents the total breakdown thereof when the solvent is removed, and, according to the authors, leads to the formation of voids or micropores. The properties of these traditional porous polyester products will be discussed in greater detail below, but it may be mentioned at this point that they have a comparatively low pore volume (e.g., volume of pores per unit mass of material) and consequently a low water absorption and water retention capacity.

[4] Dye rate is that rate at which dyestuff leaves the dyebath and becomes affixed to a specimen. Dye uptake is the quantity of dyestuff, usually expressed as a percentage of the weight of a yarn or fabric, which becomes affixed to the specimen during dyeing.

It is to be emphasized that the desired pore system in Weigmann et al., is not stable, as thermal treatment above 120° C. causes a drastic reduction of the relative dye uptake, and there is total collapse of the pore system at temperatures of 180° to 200° C. See Example 4.

In the United States, it is now well known that polyester fibers may be employed for certain utilities, including polyester filaments or yarns, particularly polyethylene terephthalate (PET), and that certain of these polyester fibers contain chemical additives: See U.S. Pat. Nos. 2,987,373; 3,100,675; 3,513,110 (particularly interesting because of its "open-celled structure" or significant pore space, with a pore structure of 150–5000 Å, and with a density of 60–90% of the corresponding polymer, the pore structure for polyester developed by heat-treating the material at temperatures of above 100° C., preferably 150°–220° C., and using adequate drawn-down ratios, with the optional use of a defined suitable swelling agent suggested); U.S. Pat. Nos. 3,748,844; 3,953,405 (also interesting—polyesters are disclosed having 0.05–5.0 mole percent of a substituted cyclobutane dicarboxylic acid before melt polymerization; in particular PET is modified with up to 15 mole percent of a dicarboxylic acid added additionally); and U.S. Pat. No. 3,969,462.

Metal-containing compounds are known to stabilize polyesters against heat: see U.S. Pat. Nos. 3,475,371 (stabilizers are selected from the group of lower alkyl and lower alkenyl esters of orthosilicic acid); 3,488,318 (stabilizers containing silane complexes with alkyl and alkoxy ligands); and 3,652,493 (stabilizers containing silane complexes with aryl, hydroxy, and alkoxy ligands).

Polymers are also known to be stabilized against ultraviolet light, including oxidative decay, by the employment of metal-containing compounds, acids, and other organic substances: See U.S. Pat. Nos. 3,357,944 (oxalo-bis-hydroazide); 3,821,163 (metal complex of N,N'-alkyl esters of ethylenedinitrilo tetraacetic acid); and 3,833,542 (dichloro(di-2-pyridylamine) copper II or bis(di-2-pyridylamine) copper II chloride).

Metal-containing compounds are also known to render polymers flame-resistant or flame-retardant; U.S. Pat. Nos. 1,225,414 ($Al_2O_3CO_2Na_2CO_3$); 3,342,898 (antimonite, borate, and silicate complexes; and 3,965,068 (combination of nickel and zinc salts).

Metal-containing compounds have also been employed to give polymers greater affinity to dye stuffs: U.S. Pat. Nos. 3,164,567 (metallosulfophenoxy-substituted benzoic or metallosulfobenzoic acid or ester); 3,166,531 (metallosulfophenoxyalkoxy-substituted aromatic monocarboxylic acid) and 3,264,255 (addition of 0.025-0.1% alkali metals).

Metal salts have also been employed as polymerization catalysts: see U.S. Pat. No. 2,850,483 (metal salt of a saturated aliphatic dicarboxylic acid containing 2-10 carbon atoms, the metal selected from Cd, Co, Mn, and Zn).

3. State of the Art

Among other approaches, attempts are now being made to improve the moisture regain properties of polyester fiber by chemical modification either of the entire polymer or of the fiber surface. So far, this has not been very successful technically or commercially, as we are advised.

Recent documented attempts in the art, many not prior art to the instant application within the meaning of 35 U.S.C. S102(b), have, inter alia, attempted to obtain hydrophilic properties for fibers by the following approaches:

(a) blending hydrophilic compounds with polyesters;
(b) employing a copolymerization of acrylic compounds with polyesters;
(c) irradiating polyesters; and
(d) attempting a partial hydrolysis of polyesters to obtain terminal (or end) groups which are hydrophilic: —OH, —COOH, or employing alkali or sulfonate salts of polyesters. See V. N. Sharma, "Hydrophilicity of Textile Fibers and Its Influence on Fabric Wear Properties", COLOURAGE at 23-27 (May 11, 1978) for a good summary of the state of the art.

Patent publications evidencing the state of the art are (1) German Offenlegungsschrift Nos. 2,719,019 (published Nov. 2, 1978); 2,554,124; 2,637,394; 2,757,787; 2,724,952; 2,713,456; 2,709,403; 2,706,522; 2,706,032; 2,705,210; 2,703,372; 2,207,503; 2,703,051; 2,659,616; 2,659,263; 2,657,144; 2,642,195; 2,633,838; 2,627,708; 2,625,908; 2,611,193; 2,610,626; 2,609,829; 2,607,996; 2,607,659; 2,607,071; 2,044,281 (see U.S. Pat. Nos. 3,695,992; 3,792,019; and 3,760,054); and 2,605,412; (2) Japanese Patent Publication Nos. 74,014,878; 74,729,485-Q; 74,030,711; 51,055,367; 50,107,290; 52,081,130; 52,074,020; 52,085,582; 52,096,297; 48,084,853; 48,019,093; 49,100,395; 7,203,850-R; 48,075,894; 48,093,665; 49,030,694; 49,066,991; 75,039,759; 7,317,204-R; 4,856,999-Q; 7,001,679-R; 75,012,007; 49,108,395; and 7,308,270; (3) U.S. Pat. Nos. 4,043,985; 4,101,525; 4,134,882; 4,070,342; 4,000,109; and 4,116,931; and (4) Swiss Patent Publication No. 468,213;

See also the following publications, summarizing the state of the art: first, pertaining to the recent Bekleidungsphysiologisches Institut E.V. (Sept. 27-28, 1978) at 7124 Boenigheim (Schloss Hohenstein), West Germany: (1) Hans Seghezzi, "Bekleidungsphysiologische Erkenntnisse rücken im Spiel um Marktund Verbrauchergunst immer mehr in den Vordergrund", Wirkereiund Strickerei-Technik, Bamberg, No. 12 at 705-708 (December 1978) and (2) K. H. Umbach, "Bekleidungsphysiologie heute", Chemiefasern/Textilindustrie at 42-47 (January 1979); second, other recent art (not prior art within SS102(b)-103 unless published before Dec. 12, 1976): Peter Hoffman, "A New Generation of Synthetic Fibers-Moisture-Absorbent Bayer Textile Fiber", Teintex No. 4 at 174-186 (1977); "Neue Bayer-Entwicklung: Saugfähige Acrylfasern als neue Synthesefaser-Generation", Chemiefasern/Textil-Industrie at 1045-1046 (December 1976); René Penisson, "Wege Zur Modifizierung von Chemiefasern", Lenzinger Berichte 36 at 24-34 (February 1974); Rolf Kleber, "Möglichkeiten zur Oberflächenmodifizierung synthetischer Fasern in der Textilausrüstung", Lenzinger Berichte 33 at 64-71 (December 1972); M. Preitscher and T. Robinson, "Hydrophiles Ausrüsten von Synthesefasern und deren Mischungen mit Cellulosefasern:Problematik und Prüfmethoden", Textil Praxis International at 1180-1190 (October 1976); "Hydrophiles Ausrüsten von Synthesefasern und deren Mischungen", Textilveredlung at 264-268 (1977); C. I. Simoneseu, et al., "Die Pfropfung von Polyäthylenterephthalat unter elektrischen Entladungen bei hohen Frequenzen", Rev. Roum. Chim. 22 (6) at 911-921 (1977); J. J. Choi, C. K. Lee, and K. J. Lee, "Radiation grafting of Hydrophilic Monomers onto Polyester", J. Korean Nucl. Soc. 5 (2) at 103-114 (1973); G. Gaussens and F. Lemaire, "Semiindustrial Production and Properties of Radiochemically Treated Hydrophilized Synthetic Textiles", Rev. Gen. Caout. Plast. 50 (11) at 911-915 (1973); G. Gaussens and F. Lemaire, "Hydrophilic Polyamide and Polyester Textiles by Grafting", Inf. Chim. 119 at 207-210 (1973); D. Zyska, A. Michaltska, "Studien der hydrophilen Behandlung von Synthesefasergeweben", Prace Inst. Wlok. 16 at 201-208 (1966); T. Okada, "Strahlungsinduzierte Modifizierung von Fasern", C. A. 70 (22) at 97823b (1969); K. Okada, "Strahlungs-Pfropfpolymerisation von hydrophilen Monomeren auf Polyesterfasern", C. A. 72 (18) at 91366 (1970); "Saugfähige Textilfaser:Eine neue Generation der Synthesefasern", Wirkerei-und Strickerei-Technik, Coburg, No. 9 at 442-445 (September 1977); F. Gelejietal, "Modifizierung der elektrostatischen Aufladung, der Anfärbbarkeit und der mechanischen Eigenschaften von Synthesefasern durch Pfropfen", Lenzinger Berichte 33 at 199-207 (December 1972); Charles Sármány et al., "Eine neue hydrophile Polamidfaser", Lenzinger Berichte 44 at 85-89 (1978); J. Hoigne et al, "Strahlung-schemische und radikalische Modifikation synthetischer Fasern", Textilveredlung 5 (5) at 400-406 (1970); M. Preitscher et al, "Hydrophiles Ausrüsten von Synthesefasern und deren Mischungen mit Cellulosefasern-Problematik und Prüfmethoden", Textil Praxis International at 1180-1190 (October, 1976); T. Robinson, "Hydrophiles Ausrüsten von Synthesefasern und deren Mischungen", Textilveredlung 12 (6) at 264-268 (1977); R. Teichmann, "Durch Pfropfpolymerization realisierbare Eigenschaftsverbesserungen an textilen Substraten:Eine Literaturübersicht", Faserforschung und Textiltechnik 26 (2) at 66-88 (1975); V. Hochman, "Die Anwendung licht-und elektronenmikroskopischer Methoden zur Untersuchung der Morphologie synthetischer Fasern", Faserforschung und Textiltechnik 27 at 417–424 (1976); W. O. Statten, "Polymer Texture: The Arrangement of Crystallites", J. of Polymer Science 16 at 143–155 (1959); W. O. Statten, "Crystallite Regularity and Void Content in Cellulose Fibers As Shown by Small-Angle X-Ray Scattering", J. of Polymer Science 22 at 385–397 (1956); W. O. Statten, "Microvoids in Fibers as Studied by Small-Angle Scattering of X-Rays", J. of Polymer Science 58 at 205–220 (1962); H. Domimetsch, "Zur Ausbildung der Faserstruktur beim Strecken von Polyä thylenterephtalatfilamenten", Chemiefasern/Textilindustrie at 1086–1092 (December 1976); Hans-Dietrich Weigmann, et al., "Die thermische Stabilität von lösungsmittel-induzierten Strukturänderungen in Polyesterfasern", Melliand Textilberichte at 470–473 (June 1976); M. Sutton, et al., "Résultats Relatifs a l'etude des Structures Poreuses des Fibres Textiles en Microcopies Optique et Electronique", Bull. Sci. Inst. Textiles France 24 at 763–781 (1970); H. D. Weigmann, et al., "Interactions of Non-aqueous Solvents with Textile Fibers; Part IV—Effects of Solvents on the Mechanical Properties of Various Textile Yarns", Textile Research Institute at 165–173 (March 1974); B. H. Knox, et al., "Interactions of Nonaqueous Solvents with Textile Fibers; Part V—Application of the Solubility Parameter Concept to Polyester Fiber-Solvent Interactions", Textile Research Institute at 203–217 (March 1975); H. D. Weigmann, et al., "Fiber Solvent Interactions and Dyeing Behavior—Progress Report No. 27—Aug. 1, 1976, to Nov. 30, 1976", Textile Research Institute, Princeton, N.J. (1977); H. D. Weigmann, et al., "Fiber Solvent Interactions and Dyeing Behavior—Progress Report No. 26—Apr. 1, 1976 to July 31, 1976", Textile Research Institute, Princeton, N.J. (1976); A. S. Ribnick, et al., "Interactions of Nonaqueous Solvents with Textile Fibers—Part II—Isothermal Skrinkage Kinetics of a Polyester Yarn", Textile Research Institute Journal 43 at 176–183 (March 1973); A. S. Ribnick, et al., "Interactions of Nonaqueous Solvents with Textile Fibers—Part III—The Dynamic Shrinkage of Polyester Yarns In Organic Solvents", Textile Research Journal 43 at 316–325 (June 1973); L. Rebenfeld, "Das Verhalten von Textilfasern unter Einfluss chemischer Behandlungen", Lenzinger Berichte 40 at 22–29 (1976); H. D. Weigmann, et al., "Interactions of Nonaqueous Solvents with Textile Fibers; Part VII—Dyeability of Polyester Yarns After Heat and Solvent-Induced Structural Modifications", Textile Research Journal 46 (8) at 574–587 (1976); H. D. Weigmann, et al., "Pulse Propagation in Polyester-Solvent Systems", J. of Applied Science 20 at 2321–2327 (1976); "Bayer-Textilfaser— Eine neue Generation Acrylfaser tritt an", Textil-Wirtschaft at 25 (Nov. 25, 1976); "Bayer A. G.—Absorptive Fiber for a Feeling of Comfort—Sensationelle Neuentwicklung auf Acryl-Basis", Textil-Mittelungen 31 (141) at page 1 (Nov. 23, 1976); "Eine neue Faser von Bayer", Frankfurter Allgemeine Zeitung at 7 (No. 264, Nov. 23, 1976); and "Neue saugfähige Acrylfaser", Melliand Textilberichte at 11–12 (January 1977).

In the process of Toray, British Pat. Specification No. 1,285,584 (corresponding to U.S. Pat. No. 3,682,846), the hydrophilic properties are obtained by the addition of 0.4–5 wt. percent polyalkylene ether and 0.3–3 wt. percent of a surfactant metal salt to the polyester resin. The metal salts disclosed in the patent are salts of carboxylic acids, phosphonic acids, or sulfinic acids. At any rate, salts of phosphonic and sulfinic acids can be disregarded; they are not related with the oxalato complexes to be used according to the instant invention, which are described in great detail, infra. There is little similarity between the carboxylic acid salts of British Pat. Specification No. 1,285,584 and the oxalic complexes used in the instant invention. The carboxylic acid salts used in the Toray process must have surfactant properties and have at least one hydrophobic group, e.g., an alkyl group, in the molecule. Consequently, long chain fatty acid salts, e.g., sodium, potassium or zinc salts of caproic, stearic, pelargonic and nonadecyclic acid are used. Most importantly, Toray teaches only simple carboxylic acid salts. By contrast, the additives of the instant invention are oxalato complexes, not possessing any surfactant properties, and do not contain alkyl residues. Simple oxalate salts were proved to be ineffective in the instant invention (see Example 1, infra).

Second, the metal salts in British Pat. Specification No. 1,258,584 are used in combination with polyalkylene ether. As sole additives, they are ostensibly ineffective. By contrast, the process of the instant invention, aside from the added oxalato complexes, requires no further additives.

Third, Toray products allegedly have pores of 0.01–3 micron diameter. This range coincides only partly with the pore size range of the hydrophilic polyester according to the instant invention, which has many pores less than 0.03 micron (300 Å). See FIG. 8 herein.

Fourth, the Toray products are said to have a pore volume of 0.5–10 percent, which is considerably less than the pore volume of hydrophilic polyesters according to the instant invention, which is about 30 percent of the total volume of the fiber. Additionally, the Toray patent specification does not indicate that the Toray products exhibit capillary condensation. The Toray products do not have measurable capillary condensation and have moisture regain of less than about two percent. In contrast to the products of Toray, the products according to the instant invention have a surface wettability (drop test) comparable to that of unmodified polyester. The Toray product, on the other hand, has a substantially higher surface wettability. In contrast to the Toray products, the products according to the instant invention have no antistatic properties. Finally, based on some indications in the Toray applications, the presence of pores having a diameter of less than 0.03 micron in the Toray product is doubtful.

Prior to the instant invention, the best attempts to obtain a hydrophilic polyester having the desired effects were obtained by physical modification of the fiber structure, e.g., by increasing the fiber surface capable of absorption. Melliand Textilberichte at 11–12 (January 1977) describes the structure principle of such a fiber, which has apparently already been realized for polyacrylonitrile fibers. Said polyacrylonitrile fibers consist of a core comprising a large number of fine capillary pores and a dense skin having a plurality of fine channels able to transport water laterally into the porous fiber core. The purpose of the skin is to protect the inner pore system and insure trouble-free processing.

German Offenlegungschrift No. 25,54,124 (published June 8, 1977, and not prior art under 35 U.S.C. §102(b) to the instant application) describes a process for obtaining hydrophilic polyacrylonitrile fibers by a dry spinning process, whereby 5 to 50 weight percent of a hydrophilic compound liquid (based on the total weight of the solution) is employed having a higher boiling point than the spinning solvent used, (1) being readily miscible with the spinning solvent and with water and (2) constituting a nonsolvent for the polymer to be spun. This compound is added to a suitable spinning solvent, such as dimethyl acetamide, dimethyl sulfoxide, N-methylpyrrolidone or dimethyl formamide. Cited examples of said liquids are: alkyl ethers and esters of high boiling alcohols, esters, and ketones; preferably use is made of glycerine. The resulting filaments have a skin/-core structure, a porous core with average pore diameters of 500 to 1000 nm (=5000 to 10,000 Å), a moisture regain of about 2 to 5 percent (at 65 percent relative humidity and 21° C.) and a water retention capacity of 10 to 30 percent.

Fibers of a skin/core structure dry-spun from acrylonitrile polymers with a moisture regain of at least 7 percent (at 65 percent RH and 21° C.) and a water retention capacity of at least 25 percent are described in German Offlegungschrift No. 26,07,071 (published Aug. 25, 1977, not prior art under 35 U.S.C. §102(b) to the instant application). These fibers are obtained by spinning an acrylonitrile polymer containing carboxyl groups from a solvent to which has been added 5 to 50 weight percent (referred to the total weight of the solution) of a compound whose boiling point is higher than that of the spinning solvent. Furthermore, the compound is miscible with water and the spinning solvent and does not dissolve the copolymer. The freshly spun yarn is washed to remove the compound added to the solvent and converting all or part of the carboxyl groups to the salt form.

This process of modifying polyacrylonitrile to improve hydrophilic properties is not technologically suitable to improve the hydrophilic properties of polyesters, since, on a production basis, polyesters are melt spun at close to 300° C. Polyester is spun under much more critical conditions than polyacrylonitrile, which is dry spun from organic solvents at comparatively low temperatures. Moreover, unmodified polyacrylonitrile already has a comparatively high moisture regain of about 1.5 percent. Unmodified polyester on the other hand has a much lower moisture regain of only about 0.3 to about 0.6 percent.

SUMMARY OF THE INVENTION

We have found surprisingly that the novel hydrophilic polyester fibers of the invention can be obtained according to an especially suitable process, comprising:
(a) melt spinning a polyester mass comprising a suitable polyester blended with an effective amount (generally from about 1 to about 20 weight %, and preferably 10 weight %) of one or more of the oxalato complexes of the general formula $M_n[Z(C_2O_4)_m]$, wherein:
(1) M is at least one of the ions Li, Na, K, Rb, or Cs;
(2) Z is one or more complex-forming central atoms from the group Mg, Ca, Sr, Ba, Zr, Hf, Ce, V, Cr, Mn, Fe, Co, Ni, Cu, Zn, Cd, B, Al, Ga, In, Sn, Pb and Sb;
(3) n ≈ 1, ≈ 2, ≈ 3, or ≈ 4; and
(4) m ≈ 2, ≈ 3, or ≈ 4, where ≈ means "about"
(b) drawing the resulting yarn; and
(c) hydrosetting the drawn yarn for an effective amount of time at a suitable temperature (ranging generally from about 90° to about 170° C.) in the presence of liquid water.

Melt spinning and drawing of the oxalato complex-containing polyester to be used according to the invention is carried out under close to conventional conditions for polyester fiber manufacture, using traditional conventional equipment. Hydrosetting is performed for a time sufficient to build up and to stabilize the pore system and also to stabilize the hydrophilic properties of the filaments. Depending on the hydrosetting temperature, oxalato complex, and polymer selected, the effective time in the hydrosetting step may generally range from at least about one minute to about one hour for continuous hydrosetting, or longer if desired. Batch hydrosetting times may run even longer.

According to the invention, the range and stabilization of hydrophilic properties of the polyester is obtained by hydrosetting under specific conditions. Hydrosetting is performed in presence of liquid water (e.g., immersing the yarn in water) at temperatures preferably ranging from about 120° C. to about 140° C., most preferably about 140° C., and if a continuous manner is used, preferably with a residence time of about one to ten minutes. Hydrosetting may be performed continuously or in batch, although it should be performed continuously for commercial reasons.

Although we are not limited in our invention to the validity of the herein described theory, the hydrophilic properties of the polyester are the surprising result of an unusual pore system within the fiber, which has the property of unusual wettability, one way of formation of which is the addition of the oxalato complex to the polymer mass components, at least portions of which are retained by the polyester. One embodiment of the invention employing 10 percent by weight $K_3Al(C_2O_4)_3$ in polyethylene terephthalate (PET) achieves not only remarkable moisture regain properties, but a "dry" and "harsh" hand like cotton, and favorable flame retardant properties.

Compared with the customarily utilized absorption mechanisms, e.g., with hydrate formation, there are, aside from the substantial absorption quantity, still further positive effects, e.g., high absorption and desorption rate, increasing absorption with increasing temperature, no swelling, and finally, no unfavorable heat effects. Depending on concentration and texture of yarn, the yarn embodiment of the invention (Example 17) utilizing 10% by weight $K_3Al(C_2O_4)_3$ in the initial PET mass components has the following drying time relative to the following fibers:

| PET Polyester | : | PET with 10% $K_3Al(C_2O_4)_3$ Starting Material | : | Wool | : | Cotton |
|---|---|---|---|---|---|---|
| 1.0 | : | 1.5 | : | 2.0 | : | 2.5 |

Moreover, the invention relates to a novel reagent for use in a process for the manufacture of hydrophilic polyester fibers having a moisture regain of at least about 2% measured at 40° C. and a relative humidity of 92%, which reagent comprises one or more of the suitable oxalato complexes indicated above. Preferably, the reagent comprises the oxalato complex suspended in a suitable material, most preferably the diol or phenol employed in the preparation of the homo- or copolyester. For example, if the suitable polyester is chosen to be polyethylene terephthalate (PET), the suspension moiety is ethylene glycol. Preferably, the suspension contains from about 20% to about 40% by weight of oxalato complex, and preferably the suspension is added to the ester interchange and/or autoclave vessels in the manufacture of the polyester.

BRIEF DESCRIPTION OF THE DRAWINGS

The following Figures are employed in Examples 16–17:

FIG. 8 is a graph plotting pore volume against pore radius for yarn with 10% $K_3Al(C_2O_4)_3$ according to the invention in the starting PET, Cotton, PET, and 50% PET/50% Cotton.

DESCRIPTION OF THE PREFERRED EMBODIMENTS

Figure 1:
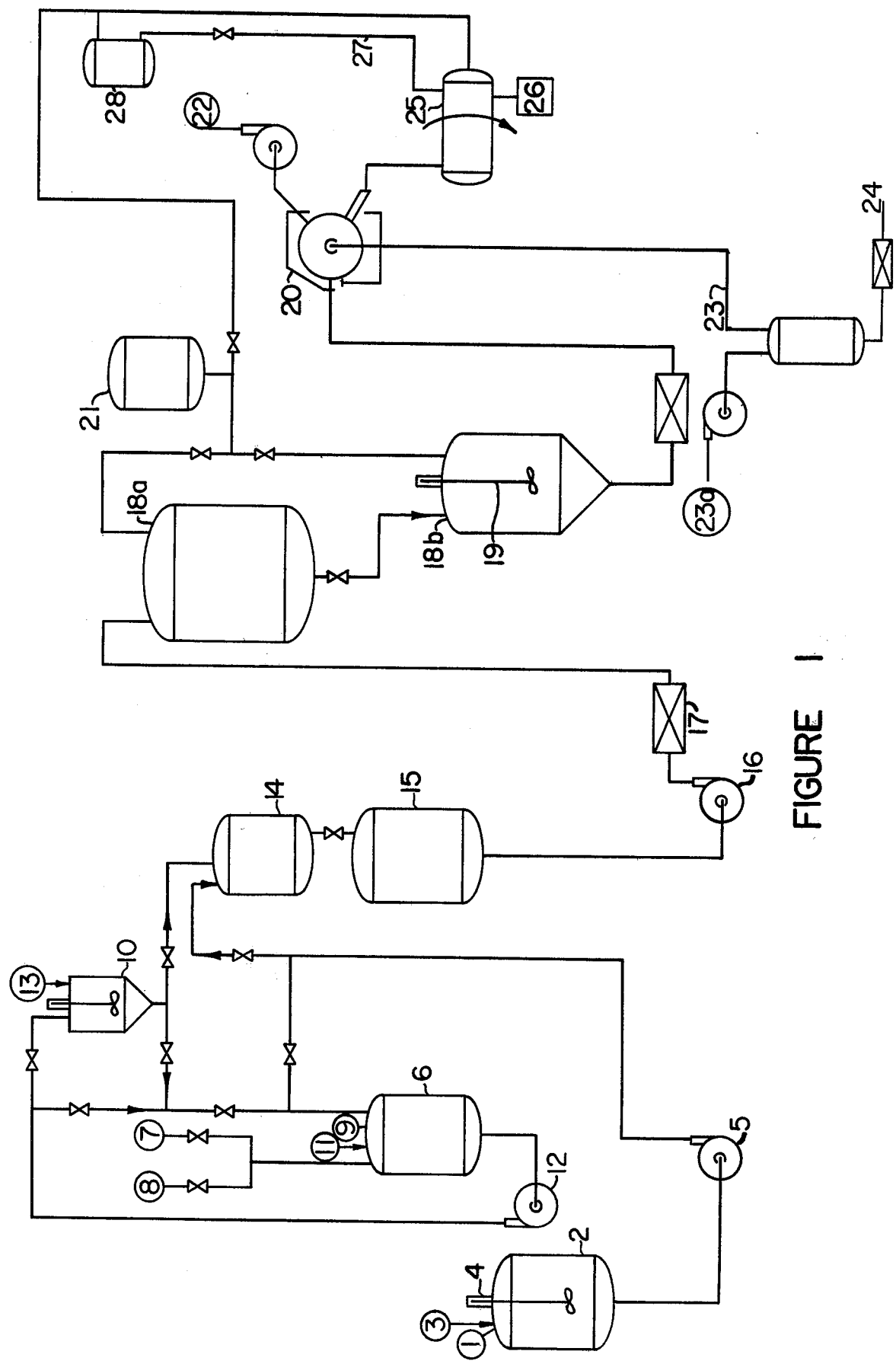
FIG. 1 represents an overall schematic flow diagram of a pilot plant for the preparation of $K_3Al(C_2O_4)_3$ from $Al(OH)_3$, KOH and oxalic acid.

A new hydrophilic polyester fiber has been found, which is produced by incorporating from about 1% to about 20% by weight of a suitable oxalato complex in the polyester mass components; the new fiber is characterized by a pore system exhibiting a moisture regain of at least about 2% at 40° C. and 92% relative humidity, which is the result of capilliary condensation. The proportion of moisture regain due to the capillary condensation is at least about 25%.[5] In one embodiment of the invention, that employing in PET starting materials 10% by weight of $K_3Al(C_2O_4)_3$ as the oxalato complex, the novel polyester exhibits a moisture regain as high as about 7–9% at 40° C. and 92% relative humidity. The novel polyester after hydrofixation contains active portions of suitable oxalato complex(es) sufficient to effect the moisture regain properties within the scope of the invention. By active portion, it is meant the entire complex, fractions or constituents thereof, and any materials from reaction of these constituents with the polymer mass components. For example, using $K_3Al(C_2O_4)_3$ in PET starting materials, the active components would include $K_3Al(C_2O_4)_3$, the elements K and Al, compounds obtained by side reactions of $K_3Al(C_2O_4)_3$ with PET, etc. These active portions in the final hydrophilic material are easily measurable by one skilled in the art by using a solvent which dissolves the polymer (for example, PET), but does not dissolve the active portions. The residue precipitates, or is otherwise separated, and is analyzed by known methods for metals, carbon and oxygen content.

[5] Capillary condensation is a phenomenon resulting from the fact that moisture tends to condense more easily over a curved surface than over a flat surface.

The present invention has successfully led to a new polyester fiber type which combines the advantages of conventional polyester fibers with many of the good properties of native fibers, even surpassing them in some respects. Special emphasis is placed on the fact that the pore system and the hydrophilic properties are stable within the scope of the invention, i.e., retained during conventional further processing and utilization.

The hydrophilic polyester fibers of the invention have outstanding characteristics. Compared with standard polyester types, they have unusual hydrophilic properties expressed in particular by high moisture regain, a high moisture perception limit (the moisture perception limit is the minimum moisture content of a specimen at which the specimen may be perceived to be moist or clammy or not dry) and high water retention. With wool and cotton, moisture regain takes place via hydration, which, in turn, is combined with a positive heat effect. The result is that at higher body temperature producing perspiration, the released hydration heat of wool or cotton causes the body temperature to rise.

By contrast, moisture regain with the hydrophilic polyesters of our invention is explainable by the property of capillary condensation, and proceeds without hydration heat. Another advantage of the polyester fibers of the invention over wool and cotton is that, as previously mentioned, they can regain increasing amounts of moisture at increasing temperature. Finally, mention should also be made of the high rate of moisture release and of the fact that the moisture regain of the hydrophilic polyester fibers of the invention does not cause swelling. This has a positive effect on the drying of the textile material.

The term "suitable polyester", or just "polyester" as used herein refers to both homo- and co-polyesters known by those in the art. Examples of said polyesters are those which can be obtained by reacting one or more of the following listed acids or their ester-forming derivatives with one or more bivalent or multivalent aliphatic, alicyclic, aromatic or araliphatic alcohols or a bisphenol. Typical acids are adipic acid, pimelic acid, suberic acid, azelaic acid, sebacic acid, nonane dicarboxylic acid, decane dicarboxylic acid, undecane dicarboxylic acid, terephthalic acid, isophthalic acid, alkyl-substituted or halogenated terephthalic acid, alkyl-substituted or halogenated isophthalic acid, nitro-terephthalic acid, 4,4'-diphenyl ether dicarboxylic acid, 4,4'-diphenyl thioether dicarboxylic acid, 4,4'-diphenyl sulfone-dicarboxylic acid, 4,4'-diphenyl alkylenedicarboxylic acid, naphthalene-2,6-dicarboxylic acid, cyclohexane-1,4-dicarboxylic acid and cyclohexane-1,3-dicarboxylic acid. Typical diols or phenols suitable for the preparation of these homo- and co-polyesters are: ethylene glycol, diethylene glycol, 1,3-propanediol, 1,4-butanediol, 1,6-hexanediol, 1,8-octanediol, 1,10-decanediol, 1,2-propanediol, 2,2-dimethyl-1,3-propanediol, 2,2,4-trimethylhexanediol, p-xylenediol, 1,4-cyclohexanediol, 1,4-cyclohexane dimethanol, and bis-phenol A. Preferred are polyesters and copolyesters of terephthalic acid, especially polyethylene terephthalate (PET).

The polyester fibers of the invention have a stable, readily water-wettable and extensive micropore system, with open micropores, that is, connected with one another, as well as with the fiber surface. Photographs from a scanning electron microscope clearly record the presence of pores, but are relatively ineffective in defining pore size description, particularly in the case of micropores. The concept "micropores" is not used uniformly in the literature, so that herein, we will refer to pores with a radius of less than 30 nm (300 Å) as "micropores". In contrast to macropores with a radius larger than 30 nm, micropores cannot be detected under a light microscope; they can be detected under an electron microscope only by using special preparation techniques. Suitable characterization methods are capillary condensation, X-ray diffraction, mercury porosimetry and finally density measurements combined with microscopy.

In an especially preferred embodiment of our invention, wherein a hydrophilic polyester contains about 10% by weight of the complex $K_3Al(C_2O_4)_3$ in the starting materials, or PET/$K_3Al(C_2O_4)_3$ yarn, this polyester is found to possess a system of pores with radii from 50 to 5000 Å. The majority of pores have radii in the range of 50–400 Å, and capillary condensation begins at about 80% relative humidity; this is about the theoretically expect value (infra). See FIG. 8, comparing the remarkable pore volume (as a function of pore radius) of yarn containing 10% by weight $K_3Al(C_2O_4)_3$ in the starting PET materials to cotton, yarn made of PET, and a 50%/50% by weight blend of PET and cotton. Pore volume depends on process conditions, but is usually about 0.25 cm$^3$/g, as against normal yarns with about 0.02 cm$^3$/g. Both micro- and macropore structure apparently influence water retention capacity. Both the micropores and macropores are interconnected to one another as well as to the fiber surface. The majority of these pores are non-spherical and are longitudinally oriented parallel to the fiber axis.

The exact mechanism of pore formation is not clearly understood at the present time. A stable pore system develops during hydroheatsetting (which may be referred to herein as simply "hydrosetting" or "HHS"), i.e., HHS refers to any hydroheatsetting step using liquid water. The average properties of the pore system of the yarn containing 10% $K_3Al(C_2O_4)_3$ in the PET starting materials before and after hydroheatsetting are as follows:

TABLE 1

| | PET | PET + 10% $K_3Al(C_2O_4)_3$ in Starting Materials | | |
|---|---|---|---|---|
| | | After Drawing Fiber (staple) | After Drawing, Filament | After HHS, Both Fiber & Filament |
| Pore Volumn (cm$^3$/g), 50–150Å | 0.01 | 0.01 | 0.06 | 0.10 |
| Pore Volumn (cm$^3$/g), 50Å–2μ | 0.03 | 0.03 | 0.1 | 0.25 |
| Density (g/cm$^3$) | 1.4 | 1.4 | 2.3 | 1.2 |
| Moisture Regain (%), 40° C./92% RH | 0.5 | 2 | 7 | 8 |

For a given pore system developed according to the invention, we have found that with the yarn containing about 10% $K_3Al(C_2O_4)_3$ in the starting PET materials, that moisture regain is almost directly proportional to $K_3Al(C_2O_4)_3$ content, and that about 10% additive of $K_3Al(C_2O_4)_3$ is sufficient to reach the desired moisture properties. The absolute level of moisture regain is apparently less important for wearing comfort than is the difference between moisture regain at standard conditions (20° C./65% R.H.) and at constant conditions of 34° C./92% R.H., which represent the body conditions near the skin during periods of perspiration. Therefore, the difference between the moisture regain under the two sets of conditions represents the amount of moisture which a fiber may absorb during periods of perspiration. The following data compare the moisture regain of various fibers under the two sets of conditions:

TABLE 2

| | Moisture Regain, % | | |
|---|---|---|---|
| Fiber | 20° C./65% R.H | 34° C./92% R.H. | Δ MR |
| Normal PET | 0.3 | 0.5 | 0.2 |
| PET with 10% $K_3Al(C_2O_4)_3$ in Starting Materials | 1.0 | 8.0 | 7.0 |
| Cotton | 6.2 | 10.0 | 3.8 |
| Wool | 15.0 | 22.0 | 7.0 |

The data demonstrates that the above-mentioned PET/$K_3Al(C_2O_4)_3$ yarn is capable of absorbing much more moisture during periods of perspiration than even cotton and approximately the same amount as wool. This represents a remarkable advance in the synthetic textile art.

A second important factor when concerning comfort is the moisture perception limit, which may be defined as the minimum moisture content at which a textile specimen feels moist or clammy or not dry. The limit may be determined by gradually increasing the moisture content of a textile until one senses the wetness associated with the sample. The process may then be reversed, and the moisture content decreased until the textile is perceived to be dry. Tests with each of four persons not cognizant of the identity of each of the normal PET, PET with 10% $K_3Al(C_2O_4)_3$ in starting materials, cotton and wool samples above show that the moisture perception limit of normal PET is about 0.4%, of wool about 19%, of cotton about 8%, and of the yarn according to the invention containing 10% $K_3Al(C_2O_4)_3$ in PET starting materials about 7 to about 11%, under experimental conditions which reflect various drying and finishing conditions. Comparing this data to moisture regain levels under standard conditions reveals that PET/$K_3Al(C_2O_4)_3$ yarn is capable of absorbing more moisture than either cotton or wool before being perceived as moist or clammy or not dry. Furthermore, during periods of heavy perspiration and subsequent drying, PET/$K_3Al(C_2O_4)_3$ yarn reaches a point at which it feels dry to the touch quicker than either cotton or wool.

The time required for moisture to wick up 2 mm in various fabrics is: Cotton, less than 10 sec.; 50% cotton/50% PET, less than 10 sec.; 100% PET, about 30 min.; and PET/$K_3Al(C_2O_4)_3$ yarn, more than 24 hours. PET/$K_3Al(C_2O_4)_3$ yarn also does not absorb and disperse drops of water. The tests indicate that the hydrophilic polyester of our invention is as wettable as wool and not as wettable as cotton.

Capillary condensation is a very important measure of the effectiveness of a particular pore system, as by definition water vapors tend to condense more easily over a curved surface than over a flat surface. Furthermore, it may well be the basis for a practical utilization of the pore system, especially in the area of wearing hygiene.

According to the law of Helmholtz-Thomson, capillary condensation of a wetting liquid will start in a capillary with a radius of curvature r when the partial pressure of the vapor of the liquid is greater than $P_r$, i.e., wherein $(Pr/P\infty)$ is less than 1, in the following equation:

$$\frac{Pr}{P\infty} = \exp\left(-\frac{2M\sigma}{RT\rho r}\right), \quad (1)$$

wherein:

$P_r$ = vapor pressure over a curved area of radius r;
p = vapor pressure over a plane area;
$M, \sigma, \rho$ = molecular weight, surface tension and density of the liquid;
R = gas constant; and
T = absolute temperature.

Assuming perfect or ideal wettability within the pores ($\beta = 0°$, COS $\beta = 1$, see (2) below), and based on numerical calculations, it follows that capillary condensation of water takes places at 20° C., when, at the listed relative humidities (RH) the capillary radii r are less than the capillary radii listed below and absolute wetting is achieved:

| R.H. % | 35 | 70 | 80 | 83.5 | 90 | 93 | 97 |
|---|---|---|---|---|---|---|---|
| r Å | 10 | 30 | 47 | 60 | 100 | 150 | 350 |

Thus, to achieve capillary condensation at a relative humidity of 90%, the capillaries must have radii of 10 nm (100 Å) or less. In the case of imperfect wetting (boundary angle $\beta$ greater than 0°) the above formula may be extended as follows:

$$\frac{Pr}{P\infty} = \exp\left(-\frac{2M\sigma \, COS\beta}{RT\rho r}\right) \quad (2)$$

wherein $\beta$ is the wetting angle between the liquid and capillary, e.g., a measure of wettability.

Corresponding smaller radii will then be required to obtain capillary condensation. It must be noted that with unmodified polyester and water the wetting angle is about 80° (T. G. Grindstaff, Text. Res. J. at 958 (1969) and thus cos $\beta = 0.2$. It follows therefrom that with unmodified wettability, capillary condensation will only take place when the pore radii are smaller by a factor of 5 than the above cited value. With absolutely nonwetting liquids ($\beta = 90°$ or $90° \leq \beta \leq 180°$) there is no capillary condensation.

For more detailed discussions of capillary condensation, reference may be made to standard physics and physical chemistry textbooks, e.g., A. W. Adamson, PHYSICAL CHEMISTRY OF SURFACES, Intersciences Publishers, 2nd ed., at 637–641 (1967); J. J. Bikerman, PHYSICAL SURFACES, Academic Press, New York, at 328, 346 and 362 (1970); E. A. Flood, THE SOLID GAS INTERFACE, Marcel Dekker Inc., New York, 2 at 1029–1045 (1967); R. Brdička GRUNDLAGEN DER PHYSIKALISCHEN CHEMIE, 11th Edition, VEB Deutscher Verlag der Wissenschaften, Berlin, at 551 to 553 (1972); H. Franke, LEXIKON DER PHYSIK (3rd Edition), at 776–779; Fränkische Verlagshandlung Stuttgart, Germany; and E. Manegold, KAPILLAR-SYSTEME, 1 (Grundlagen) Strassenbau, Chemie und Technik Verlagsgesellschaft mbH, Heidelberg, Germany (1955).

Micropores can be detected by means of continuous small-angle X-ray scattering. Normally, for the characterization of synthetic fibers by small-angle X-ray scattering, use is made of the discrete small-angle reflexes. They are produced by the periodically alternating crystalline and amorphous regions within the sample. Depending on the reciprocal arrangement of these regions, a 2-point or 4-point diagram is obtained. In addition to these discrete small-angle reflexes, polyester fibers with non-periodically ordered regions of deviating electron density also yield a continuous small-angle scatter. A pronounced small-angle scatter is obtained when these regions of deviating electron density represent voids (for details, reference is made to the literature cited infra). The hydrophilic polyester fibers of the invention exhibit such a pronounced continuous small-angle scattering.

The pore system of the hydrophilic polyester fibers according to the invention can be characterized even more precisely by a quantitative evaluation of the small-angle scattering. An isotropic small-angle scattering is obtained for spherical micropores. The radius of these spheres can be determined from the angle-dependence of the intensity of the continuous small-angle scattering. Non-spherical micropores, which have a preferred direction or orientation in the specimen, produce anisotropic continuous small-angle scattering, which anisotropy supplies information of the orientation of these pores in the specimen. The angle dependence of the intensity of continuous small-angle scattering permits determination of the transverse diameter of these non-spherical pores. In a comparison of different specimens with similar pores, the intensity of the continuous small-angle scattering yields information on the relative number of pores in the specimen.

For theory, measurement and analysis of small-angle X-ray scattering reference is made to the literature, for example H. Brumberger, SMALL ANGLE X-RAY SCATTERING, Gordon and Breach, Science Publishers, New York, 1967; M. A. Blokhim, METHODS OF X-RAY SPECTROSCOPIC RESEARCH, Pergamon Press, New York, 1968; A. Guinier, X-RAY DIFFRACTION, H. W. Freeman & Co., San Francisco, 1963; H. S. Peiser, H. P. Rooksby, and A. J. C. Wilson, X-RAY DIFFRACTION BY POLYCRYSTALLINE MATERIALS, Institute of Physics, London, 1955; A. Guinier and G. Fournet, SMALL-ANGLE SCATTERING OF X-RAYS, John Wiley & Sons, New York, 1955; Zahn and Winter, Kolloid Zeitschrift 128 at 142–153 (1952); H. Kiessig, Kolloid Zeitschrift 152 at 62–74 (1957); O. Kratky, Angew. Chemie 72 at 467–482 (1960); and V. Hochmann, Faserforschung and Textiltechnik 27 (1976), No. 8, Zeitschrift für Polymerforschung, at 417–424.

Another feature by which the polyester fibers of the invention can be characterized is the pore volume as a function of the pore radius (see FIG. 8 for PET/$K_3Al(C_2O_3)$). It is very easily determined with a mercury porosimeter, which is helpful in determining pore size, radii, volume, and distribution. The technique involves submerging a porous sample into mercury and gradually increasing pressure on the system to force Hg into the pores. Since the force required to fill the pore is inversely proportional to the pore radius, a measure of pore size distribution may be obtained by monitoring the change in volumn of Hg (i.e., change in pore volume) as a function of pressure. Pores with radii between 5 nm and 50,000 nm (50 Å to 500,000 Å) can be determined, thus micropores as well as macropores can be determined.

Density measurements may be used to verify the information obtained by Hg porosimetry and X-ray scattering. Using the pore volume measured by Hg porosimetry, the theoretical density of the polymer may be calculated. The actual density of the material may then be measured in a suitable gradient liquid (e.g., carbon tetrachloride and heptane). We have found that the calculated density and the measured density agree within experimental limits of error, indicating that the data obtained from Hg porosimetry and X-ray scattering techniques are reliable.

For theory, procedure and analysis of the mercury porosimetry, reference is also made to the literature, for example H. Juentgen and M. Schwuger, Chem. Ing. Techn. 38 at 1271–1278 (1966); and E. F. Wagner, Chemiefasern 8 at 601–606 (1967).

The pore system can also be identified by density measurement. The presence of a pore system in a specimen is identified via conventional density measurements in a gradient of [e.g.] carbon tetrachloride and heptane, provided the gradient liquid cannot penetrate the pore system, because it is closed off to the outside or because the pore walls are not wetted by the gradient liquid, resulting in distinctly lower density values than those corresponding to a pure, pore-free polymer. In these cases, the total pore volume can be calculated from the density measurements. After subtracting the pore volume detectable under the microscope, the pore volume of the microscopically invisible pores is obtained.

The results of the four measuring methods, namely, capilliary condensation, small-angle X-ray scattering, mercury porosimetry, and density measurement prove conclusively that the fibers of the invention have an extensive system of pores accessible from the outside, readily wettable by water, whose pore radii mainly measure essentially less than 30 nm.

Moreover, the permanence of the hydrophilic properties is characteristic for the polyester fibers of the invention. The pore system is considered herein by applicants as stable in the meaning of the present invention, provided it withstands at least one washing and subsequent drying in air at 100° C. These are minimum requirements; the pore system of the fibers of the invention is, however, much more stable; it is stable under customary use and processing conditions such as texturing, hot air setting (e.g., 1 minute at 190° C.), high temperature scouring and dyeing (e.g., one hour at 120° C., including hot air drying at 120° C. for 3 minutes), as well as washing at the boil, e.g., at 100° C. and 60 minutes with 5 g detergent per liter and under normal dry cleaning conditions. If the novel polyester yarn is washed at mild conditions, e.g., 25°–40° C., for 10 minutes to 30 minutes, the hydrophilic properties remain almost indefinitely e.g., more than 50 washings. Just as stable, i.e., remaining essentially unchanged, are the hydrophilic properties derived from the pore system of the polyester fibers of the invention. After performing the above measurements, the polyester fibers pursuant to our invention can be described as follows on the basis of their pore system and their hydrophilic properties.

As already stated above, the polyester fibers of the yarn embodiment of the invention containing 10% $K_3Al(C_2O_4)_3$ in the PET starting mass can absorb much more than 2 weight percent moisture at 40° C. and 92% relative humidity, approximately the minimum requirements of our invention. This total moisture regain of the hydrophilic polyester of the yarn embodiment of the invention having 10% $K_3Al(C_2O_4)_3$ in the PET mass is mainly composed of the conventional moisture regain of unmodified polyester of about 0.5% plus the moisture regain essentially attributable to capillary condensation, totaling 7%–9%. The proportion of moisture regain attributable to capillary condensation for the polyester fibers of the invention is at least about 25% of the total moisture regain, thus for a low total moisture regain it is comparatively low, e.g., 25%, and for a high total moisture regain comparatively high, e.g., about 95% (PET/-$K_3Al(C_2O_4)_3$). Preferably it is at least about 70% of the total moisture regain.

At 40° C. and 92% relative humidity, the hydrophilic polyester fibers of the yarn embodiment of the invention containing 10% $K_3Al(C_2O_4)_3$ in the starting PET mass materials have a moisture regain of up to 25 weight percent. Polyesters with a moisture regain of 5 up to 12 or 13 weight percent are generally preferred, as a compromise must be struck between the spinnability of the yarn and comfort properties. Such products can be processed without difficulties and exhibit excellent textile properties. The polyester fibers of the PET/$K_3Al(C_2O_4)_3$ yarn embodiment of the invention containing 10% $K_3Al(C_2O_4)_3$ in the PET reactants, with a moisture regain of from about 13 weight percent to 25 weight percent at 40° C. and 92% relative humidity, can also be produced without great difficulty, especially in the case of heavier deniers; however, due to their comparatively high pore volume they have correspondingly lower tenacities.

The apparent density of the fibers of the composition of the invention in case of PET is less than 1350 kg/m$^3$, preferably ranging between 1050 and 1150 kg/m$^3$.

As stated, the pore system of the polyester fibers of the novel hydrophilic polyester fibers of the invention is preferably composed of a large number of micropores and macropores. The radii of the micropores are less than 30 nm, as previously defined herein and preferably range between 5 and 15 nm. The radii of the macropores may range at least between 100 and 3000 nm. The micropore volume generally exceeds about 0.04 cc/g. The fibers of the invention preferably contain a large pore volume based upon micropores with radii ranging from 5 to 15 nm and, thereby producing a micropore volume ranging between about 0.04 to about 0.15 cc/g. The macropore volume may range from about 0.01 to about 0.10 cc/g. Products with an even greater pore volume, up to 0.5 cc/g, can also be obtained; however, they must employ large amounts of the oxalato complex (up to about 20 weight percent) and are intended for end uses requiring no or only minimal fiber strength.

Both micropores and macropores of the polyester fibers of the invention are open, i.e., they are connected to one another as well as to the fiber surface.

The polyester fibers of the invention contain preferably nonspherical micropores, their longitudinal dimension being a multiple of the transverse dimension. As mentioned, the majority of these nonspherical pores are oriented parallel to the fiber axis.

A characteristic of the polyester fibers of the invention is that the walls of the pore system are readily wettable with water. This special quality of the pore walls, like the described pore system, is probably responsible for the hydrophilic properties of the polyester fibers of the invention.

Compared with conventional polyesters, the products of the yarn embodiment of the invention with 10% $K_3Al(C_2O_4)_3$ in the reaction mass have a surprisingly high moisture regain. In the following table are listed values for a standard polyethylene terephthalate fiber, for polyethylene terephthalate fiber according to the invention prepared with the use of 10 wt. % potassium aluminum oxalate ($K_3[Al(C_2O_4)_3]$ or $K_3Al(C_2O_4)_3$) and for wool. Measurements were performed according to German Standard (or "DIN") 54-201, entitled "Testing of Textiles—Quantitative Determination of the Constituents of Fiber Blends—General Operating Instructions", August 1975 (incorporated herein), in a constant climate of 20° C./65% RH (standard climate according to DIN German standard DIN 50-014, entitled "Atmospheric Conditions and their Technical Application—Standard Atmospheres", December 1975, incorporated herein), 20° C./92% RH, 34° C./92% RH and 40° C./92% RH (warm moist constant climate according to DIN 50-015, incorporated herein):

TABLE 3

| Fiber Type | MOISTURE REGAIN (IN WT. %) | | |
|---|---|---|---|
| | Polyethylene Terephthalate | | |
| Conditioning | Standard Type | Invention Type | Wool |
| 20° C./65% RH | 0.3 | 1.0 | 15 |
| 20° C./92% RH | 0.4 | 6.5 | 24 |
| 34° C./92% RH | 0.5 | 8.0 | 22 |
| 40° C./92% RH | 0.6 | 10.0 | 21 |

The table indicates that when conditioned, the polyester fibers of yarn embodiment with 10% $K_3Al(C_2O_4)_3$ in the reaction mass exhibit both in a standard atmosphere of 20° C./65% R.H. and at higher temperatures and higher relative humidities a substantially higher moisture regain than standard polyester types. As stated, the absolute moisture regain is less important for wearing hygiene than the difference between moisture regain at 20° C./65% R.H. and at constant conditions of 34° C./92% R.H. The reason is that constant conditions of 34° C./92% R.H. correspond to body conditions near the skin at the upper limit of the comfort range and the difference in moisture regain consequently corresponds to the moisture regain capacity of the textile material during wearing to the limit of the comfort range. As seen in the chart, for the standard polyethylene terephthalate (PET), the difference is only 0.2%, while for the hydrophilic polyester fibers of the yarn embodiment of an invention with 10% $K_3Al(C_2O_4)_3$ in the PET reaction mass, it is 7.0%. Consequently, the value is as high as for wool. In contrast to hydrophilic polyester fibers, wool absorbs less moisture with increasing temperature. This effect counteracts the wearing comfort of the textile material, inasmuch as with increasing skin temperature and consequently increasing perspiration, it is desirable that the textile material be able to absorb more, not less moisture.

Another important characteristic of the fiber of the invention is its high water retention capacity. In contrast to moisture regain, which is essentially determined by the micropore system, the water retention capacity depends both on the micropore and the macropore structure. The water retention capacity is usually determined according to German Standard (DIN) 53-814, entitled "Testing of Textiles—Determination of the Water Retentivity of Fibers and Yarn Sections", October, 1974, incorporated herein: using a wetting agent, a certain amount of the material to be checked is completely saturated with water and then centrifuged under precisely defined conditions. The centrifuged specimen is weighed, dried and weighed again. The difference between both weights represents the water retained by the specimen after centrifuging. As a rule, standard polyester has a water retention capacity of about 2 to about 5%, whereas the fibers of our invention have 10 to 50%, preferably 20-30%. The known polyesters obtained by solvent-induced structural modification have about 8.5%. The water retention capacity is also of decisive significance for the use characteristics of textiles: cotton and wool have a water retention capacity of about 40 to 50%, consequently the fibers according to the invention are in this respect on the same level as natural fibers. In this connection it should be kept in mind that wool and cotton have already regained 8 to 15% moisture during storage. All German Standards may be obtained from Beuth-Vertrieb GmbH, Berlin 30 and Köln 1, W. Germany.

A further important characteristic in the wearing comfort of textile material is the moisture perception limit. It indicates the moisture content (in percent) at which a textile specimen feels moist.

Two methods were used to determine the moisture perception limit. One of the methods uses a dried textile specimen, e.g., flat knit material, which is exposed to increasing levels of humidity. The other method uses textile specimens which have been wetted in keeping with the method to determine the water retention capacity (DIN 53-814) and are then dried in a standard atmosphere (20° C. and 65% R.H.). In both cases at least four persons checked whether the knitted materials already felt too moist, or already dry enough, so that they would no longer, or would limit wear of an undershirt made from said material. The moisture perception limit for standard polyester is about 0.4%, for wool about 19% and for cotton about 8%. The moisture perception limit for the fibers of the invention using the yarn embodiment wherein 10% $K_3Al(C_2O_4)_3$ is employed in the PET reaction mass is about 7 to about 11%. A practical consequence is that textiles from unmodified polyester have only about 0.1 weight percent moisture regain, when after storage in a standard atmosphere they are moistened to the moisture perception limit. Under the same conditions, woolen textiles regain approximately 4 weight percent moisture, but textiles from the polyester fibers of the invention regain about 8 weight percent.

Also in the terms of moisture release, the fibers of the invention also have the excellent properties about that of normal polyester. Moisture release is the property measured by the tendency of a previously wetted specimen to give up moisture in a standard atmosphere of 20° C. and 65% R.H., i.e., here it characterizes the progress with time of moisture released in a standard atmosphere of 20° C. and 65% R.H. by a specimen previously wetted according to DIN 53-814. Of particular interest here is the time required to reach the moisture perception limit. Assigning a value of 1 to standard polyethylene terephthalate, the relative value of the hydrophilic polyester of the invention is 2, wool is 2.5 and cotton is 3; in other words, the point in the drying process at which the hydrophilic polyesters of the invention feel dry is reached sooner than with wool or cotton. See Example 16.

In addition to the above discussed properties relating to hydrophilic characteristics, the fibers of the invention also possess other excellent textile properties comparable to those of standard polyester types. The fibers according to the invention can be produced in conventional deniers and exhibit for example the following textile properties:

TABLE 4

COMPARATIVE PHYSICAL PROPERTIES

|  | Hydrophilic Polyethylene Terephthalate Fiber of the Invention | Standard Polyethylene Terephthalate Fiber |
|---|---|---|
| Fineness (here dtex)* | 3.3 | 3.3 |
| Elongation (%) | 45 | 40 |
| Strength (cN/dtex)** | 33 | 42 |
| Modulus at 10% Elongation (cN/dtex)** | 10 | 12 |

*Denier represents a weight-per-unit length of any linear material. Classically, denier represents the weight in grams per 9,000 meters of length. Here it is measured in dtex, which is grams of a 10 kilometer length of filament.

**cN/dtex - Centinewton(s) per dtex, or a measure of the force required to break a yarn, for example, per unit of cross-sectional area.

As stated above, the $K_3Al(C_2O_4)_3$ additive was originally evaluated as a flame retardant for PET. An evaluation indicates the following results:

TABLE 5

COMPARATIVE FIRE RETARDING PROPERTIES

| Sample | 1 | 2 | 3 | 4 |
|---|---|---|---|---|
| $K_3Al(C_2O_4)_3$ content | 0 | 10 | 10 | 8 |
| Hydroheatset | No | No | Yes | Yes |
| High Temperature Dyeing (1 hr, 125° C.) | Yes | Yes | Yes | Yes |
| Heatset (Air, 1 min, 190° C.) | No | No | Yes | Yes |
| Household launderings before Flame Tests 60° C.) | 50 | 50 | 50 | 10 |
| $K_3Al(C_2O_4)_3$ Content After Launderings | 0 | 5.9 | 5.3 | 6.6 |
| Time of Burnings, sec |  |  |  |  |
| after 3 sec Ignition (max/avg) | 56/40 | 3/2 | 12/4 | 35/17 |
| after 15 sec Ignition (max/avg) | 40/29 | 2/1 | 2/1 | 6/3 |
| Tear Length after Burning, mm |  |  |  |  |
| after 3 sec Ignition (max/avg) | 138/86 | 15/11 | 95/42 | 248/120 |
| after 15 sec Ignition (max/avg) | 185/132 | 104/84 | 138/124 | 141/124 |
| After Glow Time, sec | 0 | 15 | 14 | 15 |
| Limiting-Oxygen Index | 21.6 | 27.2 | 26.7 | 25.3 |

All of the samples were circular knit from filament yarn into similar fabrics (about 300 g/m²). Although Sample 2 was not hydroheatset in a separate process, the high temperature dyeing served the same purpose. A similar sample which had been neither hydroheatset nor dyed at high temperature contained only 4% additive after three launderings and essentially no $K_3Al(C_2O_4)_3$ after ten washings.

The fibers of the invention have a great dye affinity and depth: the hydrophilic polyester fibers of the invention, like heretofore known microporous polyesters, require more dyestuff than standard polyester fiber types, and hence the rate of dye uptake is higher for the polyester fibers than for standard polyester fiber types. Dye depth refers to the relative lightness or darkness of dyed fabrics or yarn when compared with a control sample.

The hydrophilic polyester fibers can be obtained according to an especially suitable process by:
  (a) melt spinning a polyester mass comprising a suitable polyester blended with an effective amount (generally from about 1 to about 20 wt. %) of one or more of the oxalato complexes of the general formula $$M_n[Z(C_2O_4)_m],$$

(which hereinafter may be referred to as suitable oxalato complexes), wherein:
  (1) M = at least one of the ions Li, Na, K, Rb, or Cs;
  (2) Z = one or more complex-forming central atoms from the group Mg, Ca, Sr, Ba, Zr, Hf, Ce, V, Cr, Mn, Fe, Co, Ni, Cu, Zn, Cd, B, Al, Ga, In, Sn, Pb and Sb;
  (3) $n \approx 1$, $\approx 2$, $\approx 3$, or $\approx 4$; and
  (4) $m \approx 2$, $\approx 3$, or $\approx 4$, where $\approx$ means about.
  (b) drawing the resulting filament yarn; and
  (c) hydrosetting the drawn yarn at a suitable temperature (generally ranging from about 90 to about 170° C.) for an effective amount of time in the presence of liquid water. Filament yarns as used herein includes staple fiber tow.

As used herein, hydroheatsetting means the same thing as hydrosetting. Melt spinning and drawing of the oxalato complex-containing polyester to be used according to the invention is carried out under close to conventional conditions for the corresponding polyester without the oxalato complex, using traditional conventional equipment, with deviations for each step varying on the oxalato complex, desired end effect, and polymer employed, but each step is ascertainable for those of normal skill of in the art. A sequence of steps is disclosed in Example 17 for the manufacture of the PET embodiment of our invention having about 10% by weight $K_3Al(C_2O_4)_3$ in the starting PET materials.

According to the invention, the remarkable properties of difference in moisture regain (between 20° C./65% R.H. and 34° C./92% R.H.) and stabilization of the hydrophilic properties of the polyester are obtained by hydrosetting under specific conditions. Hydrosetting is performed in presence of liquid water at temperatures preferably ranging from 120° to 140° C., most preferably at about 140° C.

By suitable temperature, we mean any temperature effective to assure pore formation adequate to obtain at least a moisture regain of 2% at 40° C. and 92% R.H.; generally it is about 90° C. to about 170° C. but may be more or less depending on the polyester, oxalato complex, and end result desired.

It is to be noted that prior to hydroheatsetting the yarn should be properly drawn. For example, with $K_3Al(C_2O_4)_3$ in PET, a drawing rate of 400 m/min is employed, and two godets are recommended, one at about 110° C. and the second at about 170° C.

Although the oxalato complex can vary from generally about 1 percent by weight on up to 20 percent by weight in the starting polymer mass materials in ester interchange or autoclave (depending on the polymer oxalato group selected), as will be recognized by those skilled in the art, if too great an amount of oxalato complex is employed, the yarn may not be strong as desired, or may not be wear-resistant, or even worse, may not be producable, although the polymeric mass may have excellent moisture regain properties. Generally, the moisture regain properties increase functionally, if not directly proportionally, with an increase in content of oxalato complex in the starting materials, which reflect an increase in active portions of oxalato complex in the final hydrophilic polyester fibers. Hence, for a desired moisture regain of the resulting yarn, which is generally at least about 2% by weight measured at 40° C. and a relative humidity of 92%, an effective amount of oxalato salt is employed in the starting polymer mass materials just sufficient to obtain the moisture regain desired.

By effective amount of time, we mean for the oxalato complex, suitable polyester, and moisture regain desired, a time sufficient to effect a stable pore system containing active portions of the oxalato group sufficient to effect hydrophilic properties within the scope of our invention; our experiments indicate that the time may vary from about 1 minute to several minutes in continuous hydrosetting depending on the above variables. Effective times for batch hydrosetting may be longer, e.g., more than about one hour. For a given novel polyester, depending on the polymer, oxalato complex, hydrosetting temperature, etc., chosen, the effective times may be readily ascertained after routine experimentation by those skilled in the art.

By polyester fiber, we mean for the purposes of this application both polyester filament yarn and polyester staple.

An essential feature of the invention is that before hydrosetting the fibers be subjected neither to a hot air treatment above 120° C., nor to steam treatment, i.e., stabilization, hot air setting or texturing, nor to washing at temperatures below 90° C. with subsequent hot air drying. Products without the hydrosetting treatment of the invention, but subjected to the above-mentioned hot air treatment or washing, have a distinctly (about ½) lower moisture regain than the products of the invention. This also applies to the water retention capacity. Products which are first subjected to the above-mentioned hot air treatment or washing and subsequent hydrosetting exhibit only low hydrophilic properties. It follows therefrom that the time of hydrosetting, i.e., the sequence of drawing, hydrosetting and conventional thermal treatment is important.

The hydrosetting temperature as well has a decisive influence on the hydrophilic properties of the polyesters of the invention. With increasing hydrosetting temperature both moisture regain and water retention capacity increase. Using water, if hydrosetting is carried out at temperatures below 90° C., the products have a comparatively low moisture regain and a likewise low water retention capacity.

With continuous hydrosetting using water, no substantial effect on the moisture regain was observed when the duration of the hydrosetting treatment was altered from a few minutes to half an hour. Regarding shrinkage during the setting process, it was found that setting of the fibers of the invention could be accomplished either with or without tension, e.g., setting of the staple fiber, or setting of the yarn running without tension, or setting of the yarn under tension up to the shrinkage tension, for instance, on the spool. However, the water retention capacity and the volume of the macropores are significantly influenced by this. When the fiber was able to shrink freely, significantly higher values of moisture regain were obtained than for hydrosetting under shrinkage tension.

A special embodiment for hydrosetting will now become apparent to those in the art: for example, high temperature dyeing in an aqueous medium, preceded by methyl dichloride treatment at 35° C. for about 1 minute to set the yarn.

An essential feature of the invention is that hydrosetting be carried out at the given temperatures in the presence of liquid water. It is, therefore, necessary that the material subjected to hydrosetting makes contact with liquid water. The amount of liquid water is at least 30% and most preferably in excess of 100 weight percent, referred to the hydroset material. Care must be taken that the water is distributed as evenly as possible in or on the material. Water can be best applied, for example, by immersing the material in water, subsequently allowing it to drip off, or, in the alternative, by spraying the material with water.

It is not necessary that the hydrosetting medium be exclusively water. It may also contain small or large quantities of additives, for example, water soluble salts, solids or liquids miscible with water. Additives which raise the boiling point of water may, for instance, be used to carry out hydrosetting at the cited temperatures at lower pressures.

It is especially advantageous to perform the hydrosetting operation during high temperature dyeing or white tinting procedure under the above-indicated conditions. But, as outlined previously, prior hot air treatments above 120° C. and washing below 90° C. should be avoided beforehand, since this would significantly impair moisture regain and water retention capacity.

The polyester starting materials containing one or more oxalato complexes required for the process of the invention are described in detail in U.S. patent application Ser. No. 774,073, filed Mar. 3, 1977, now U.S. Pat. No. 4,169,827 and incorporated herein by reference (corresponding to German Offenlegungsschrift No. 2,628,964.5-43). They are obtained by conventionally introducing one or more oxalato complexes into the polyester mass. A suitable procedure is, among others, one where the oxalato complex is already added to the initial polyester material in one of the ester interchange or polycondensation vessels and is thus homogeneously dispersed in the forming polyester. Another possibility of incorporation consists in melting the polyester material, mixing it with the oxalato complex, followed by formation into chips which can be used for immediate processing. Another possibility is to dust the polymer chips with the finely divided oxalato complex.

It is also possible to use a bicomponent polyester fiber instead of a single component polyester or copolyester fiber. The skin and core of the fiber may contain a different polyester substrate and/or different oxalato complexes and/or different quantities thereof. Preferably, said initial bicomponent fibers have a skin consisting of an unmodified polyester, for instance, polyethylene terephthalate, and a core from an oxalato complex-containing modified polyester. Subjecting these bicomponent fibers to the process of the invention will also yield the fibers of the invention. It is surprising that this is also the case when the skin is composed of unmodified polyester. The resulting products are smoother on the outside and have the same hand as normal polyester types.[6]

[6]Hand refers to the quality or characteristic of a fabric perceived by the sense of touch, e.g., softness, firmness, roughness, etc.

The preparation of the oxalato complexes used in the instant invention is taught by K. V. Krishnamurty and G. M. Harris in Chemical Review, Vol. 61 (1961), pp. 213-246. The number of ligands is as a rule 1, 2, 3, or 4, the charge of the complex anions $-1$, $-2$, $-3$, $-4$, or $-5$ and the number of central atoms 1, whereby the number of ligands and the charge of the complex anions are determined by the coordination number and the charge of the central atom. Within the meaning of the present invention, oxalato complexes with complex anions of the type $[Z(C_2O_4)_m]^{-e}$ are understood to mean not only those complexes, whose composition is exactly stoichiometric, but also complexes with values for m and $-e$ deviating upwards or downwards from integers. This is for instance the case when a small portion of the oxalato ligands is replaced by other ligands. Such complexes may form when during or after synthesis of the oxalato complexes, alien ligands are built-in or substituted in the complex anion. The same applies correspondingly to the central atom, i.e., included within the meaning of the invention are also oxalato complexes whose cationic constituent is not composed along strictly stoichiometric lines. Consequently, here as well, the value for the central atom may deviate from an integer. This will be the case when part of the central atom is replaced by another central atom with a different coordination number or another valency. Such deviations from a precise stoichiometry occur more frequently in complex chemistry and are known to those well-skilled in the art.

The polyester masses to be used in the invention process may also contain mixtures of oxalato complexes, which instead of the stoichiometric quantity of a central atom have a corresponding amount of different central atoms. The polyester masses may of course also contain mixtures of different homogeneous or mixed oxalato complexes.

Since the values for n and m may deviate from integers, we selected the symbol $\approx$ in the formula.

For the process of the invention use is preferably made of polyesters containing an oxalato complex with one or more of the central atoms Mg, Ba, Zr, Fe, Co, Cu, Zn, Al, Sn, Cr and Sb. Preferred polyesters contain an alkali-aluminum oxalato complex of the following general formula:

$M_3[Al(C_2O_4)_3]$ or $M[Al(C_2O_4)_2]$, particularly if M is Na or K: and most particularly, $K_3[Al(C_2O_4)_3]$ (see Example 17). Other useful oxalato complexes include the following:

$K_4[Zn(C_2O_4)_3]$; $K_4[Zr(C_2O_4)_4]$; $K_4[Cr(C_2O_4)_3]$;
$K_3[Fe(C_2O_4)_3]$; $K_3[Sb(C_2O_4)_3]$; $K_2[Mg(C_2O_4)_2]$;
$K_2[Fe(C_2O_4)_2]$; $K_2[Zn(C_2O_4)_2]$; $K_2[Cu(C_2O_4)_2]$.

The compounds are complex lithium, sodium, potassium, rubidium or cesium aluminum-dioxalates or aluminum-trioxalates with coordinate tetravalent or hexavalent atoms. See Example 18. They are known and are prepared simply by precipitation of their components from aqueous solutions, for example by reaction of an aluminum sulfate solution with a lithium, sodium, potassium, rubidium or cesium oxalate solution.

As regards the preparation process and the properties of these complex salts reference is made to GMELINS HANDBUCH DER ANORGANISCHEN CHEMIE, 8th Edition, "Aluminum", Part B-1, Verlag Chemie GmbH Weinheim/Bergstr., (1933), incorporated herein.

Another process suitable for the preparation of the potassium-aluminum trioxalate salt according to which freshly precipitated aluminum hydroxide is treated with an aqueous solution of potassium hydrogen oxalate, is described in INORGANIC SYNTHESES, Vol. I, McGraw-Hill Book Co., Inc., New York and London at 36 (1939). The oxalate complexes with other central atoms to be used according to the invention are also known and adequately described in the prior art. They can be obtained by reaction of a salt of the central atom with alkali oxalate. Suitable compounds of the central atom are e.g., sulfates, chlorides, hydroxides, acetates, carbonates and oxalates. Details on the preparation of these complexes are described in the following literature citations:

D. P. Graddon, J. Inorg. and Nucl. Chem. 1956, Vol. 3, at 308-322.

Bailar et al, Inorg. Syntheses, Vol. I, at 36.

K. V. Krishnamurty et al., Chem. Rev. 61 (1961), at 213-246.

Oxalato complexes, whose preparation is not explicitly described in the cited publications can be prepared in an analogous manner. Here too, the number of alkali and alkaline earth atoms, i.e., the magnitude of n, as well as the magnitude of m is determined by the valency of the central atom. The invention also encompasses the utilization of such compounds whose composition is not precisely stoichiometeric within the meaning of the above formula and consequently compounds with values for n and m deviating upward or downward from whole numbers are encompassed in the invention.

The invention is exemplified by the following Examples, which should not be construed as limiting the broad embodiments of the invention, but are for illustration purposes only, from which those skilled in the art may depart without going beyond the teaching above or the scope of the appended claims:

EXAMPLES 1 AND 2

Preparation of a Polyethylene Terephthalate Fiber According to the Invention (a) Preparation and Grinding of the Oxalate Complex: $K_3[Al(C_2O_4)_3]$ was prepared according to the method J. C. Bailar and E. M. Jones in INORGANIC SYNTHESES 1 at 36 (1939). The resulting complex was subsequently dried for 15 hours at 150° C. and at about 10 Torr. Analytical data for the specimens which were obtained in different batches showed stoichiometric ratios between $K_{2.87}[Al(C_2O_4)_{3.02}]$ and $K_{3.36}[Al(C_2O_4)_{3.46}]$ 200 g of the dried complex were ground with 400 g ethylene glycol for 2 hours in a bead mill (PMI TM, Draiswerke, Mannheim, Germany) with 410 g quartz beads of a diameter of 1 to 3 mm. After grinding, the diameter of the largest particle of the complex in the dispersion measured about 4 μm, whereas the majority of the particles had a size of 1 μm. Subsequently, the quartz beads were separated by filtration through a screen, washed with 200 ml ethylene glycol and the dispersion diluted with the washing solution. The dispersion was allowed to stand for 72 hours in tall vessels where the particles of a diameter larger than 2 μm were largely separated by sedimentation.

(b) Polycondensation

Either (a) 600 g (Example 1) or (b) 300 g (Example 2) of this dilute dispersion with a $K_3[Al(C_2O_4)_3]$ content of either 150 g or 75 g were mixed and stirred together with the ester interchange product of 1350 g dimethyl terephthalate and 1200 g ethylene glycol and transferred to a polycondensation vessel with stirring at 30 rpm and a temperature of about 245° C. Zinc acetate (150 ppm) was used as ester interchange catalyst, 200 ppm antimony trioxide as condensation catalyst. The ethylene glycol distilled off was usable without purification for new condensations. The polycondensate contained either (a) 10 (Example 1) or (b) 5 (Example 2) weight percent $K_3[Al(C_2O_4)_3]$.

(c) Shaping

The resulting polycondensate was made into chips as usual and dried for 24 hours at 125° C. and 60 Torr. The chips were spun at 296° C. (spinning assembly temperature) to a filament yarn of IF 3.0 dtex and a total denier of dtex 150 f 48. The filament yarn was drawn at 110° C. and 170° C. by two plates at an overall ratio of 1:4.2 and subsequently twisted. In terms of light stability, lightfastness and solution viscosity, the textile data of the resulting material are very much like those of conventional polyethylene terephthalate obtained under the above indicated conditions without the addition of an oxalato complex.

(d) Batch Hydrosetting

About 15 g of each of the above materials or knitted specimens made therefrom and 200 ml water were introduced together into a 270 ml pressure-resistant vessel and placed in a Linitest unit preheated to 140° C. After a retention time of 15 minutes, the vessel was removed and in 5 minutes cooled with running water to 60°–80° C. After rinsing with distilled water, the textiles were predried for 1 hour at 100° C. in a circulating air drying oven and then dried for another 4 hours at about 120° C. and 15 mb (20 Torr) to weight constancy for the measurements.

EXAMPLE 3

Preparation of an Unmodified Polyethylene Terephthalate Fiber (Control Sample)

An unmodified polyethylene terephthalate fiber was used for comparison purposes. Polycondensation and shaping were performed as outlined in Steps b and c of Example 1.

EXAMPLE 4

Preparation of a Polyethylene Terephthalate Fiber Modified with Dimethyl Formamide (Control Example)

For comparison purposes, a polyethylene terephthalate which had been modified by treatment with dimethyl formamide according to the method described by H. D. Weigmann et al (supra) was made. The specimen was treated with dimethyl formamide for 2 minutes at 140° C. without tension, and the solvent was subsequently removed with water (15 minutes at 100° C.) and dried in air. Since the authors fail to mention a drying temperature, we dried one sample, a., at 20° C. and another sample, b., at 100° C.

The porous and hydrophilic properties of the above-described fibers according to the invention are listed in Table 6 and compared with the above control fibers.

The measuring methods are indicated by key words in Table 6. As regards the measuring procedures, reference is made to the description and the cited literature and Standards, respectively, which are incorporated herein.

EXAMPLES 5 to 15

The following examples refer to the preparation of hydrophilic polyethylene terephthalate fibers, polybutylene terephthalate fibers and copolyester fibers of terephthalic acid/adipic acid, terephthalic acid/azelaic acid and terephthalic acid/isophthalic acid, reacted with ethylene glycol. Flat-knitted material from drawn polyester or copolyester filament yarn was used. Hydrosetting was carried out in a Linitest unit for 15 minutes at 140° C.

In Table 7 are listed the polyester or copolyester materials used, i.e., polymer, oxalato complex and amount thereof in the polymer mass, as well as the moisture regain measured at 40° C. and 92% relative humidity. For comparison, the moisture pickup (regain) of an unmodified polyethylene terephthalate fiber and an unmodified copolyester fiber of terephthalic acid, azelaic acid and ethylene glycol is also listed.

TABLE 6

| Properties | Measuring Method | Dimension | Example 1 | Example 2 | Example 3 (Control) | Example 4 (Control) |
|---|---|---|---|---|---|---|
| Porosity | | | | | | |
| Pore volume r<15 nm | Hg porosimetry | cm³/g | 0.125 | 0.085 | 0.010 | (a) 0.016 |
| | | | | | | (b) 0.008 |
| r <2000 nm | Hg porosimetry | cm³/g | 0.250 | | 0.016 | (a) 0.024 |
| | | | | | | (b) 0.020 |
| r ca. 1000 nm | Microscopy | cm³/g | 0.050 | | | |
| r ca. 10 nm | Small angle X-ray | | pronounced | | slight | |
| Orientation | Small angle X-ray | | yes | | | |
| Density | Organ. gradient | g/cm³ | 1.088 | 1.242 | 1.390 | |
| Relative dye affinity | Extinction Absorp- | | 2.9 | | 0.4 | (a) 9.5 |
| (cf. H.D. Weigmann et al, supra) | tion at 250 nm. | | | | | |
| Moisture Regain at equilibrium | | | | | | |
| (based on dry weight) | | | | | | |
| at 65% RH/20° C. | DIN 54-201 | % | 1.0 | 8.0 | 0.3 | |
| at 92% RH/34° C. | DIN 54-201 | % | 8.0 | | 0.5 | |

TABLE 6-continued

| Properties | Measuring Method | Dimension | Example 1 | Example 2 | Example 3 (Control) | Example 4 (Control) |
|---|---|---|---|---|---|---|
| at 92% RH/40° C. | DIN 54-201 | % | 10.5 | 6.8 | 0.6 | (a) 1.0 |
|  |  |  |  |  |  | (b) 0.3 |
| Rate of change in moisture level (half value time) |  |  |  |  |  |  |
| from 65%/20° C. to 92%/40° C. |  | Min. | 35 |  |  |  |
| from 92%/40° C. to 65%/20° C. |  | Min. | 15 |  |  |  |
| Moisture Perception Limit |  |  |  |  |  |  |
| During wetting, rel. H. |  | % | 92 |  |  |  |
| Moisture content |  | % | 9 |  | 0.4 |  |
| During drying, drying time |  | Min. | 45 | 23 | 8 |  |
| Moisture content |  | % | 9 | 7 | 0.4 |  |
| Water retention Capacity |  |  |  |  |  |  |
| Fibers | DIN 53-813 | % | 30 | 16 | 5 |  |
| Knitted material | Analogous to |  |  |  |  |  |
|  | DIN 53-813 | % | 21 | 12 | 1 | 3 |
| Drying time |  |  |  |  |  |  |
| at 65% RH/20° C. |  |  |  |  |  |  |
| from water retention capacity to moisture perception limit in % referred to wool |  | % | 75 |  | 40 |  |

TABLE 7

| | | Oxalate Complex) | | |
|---|---|---|---|---|
| Example No. | Polyester Mass | Formula | Proportion referred to on Polyester mass wt. % | Moisture Regain at 40° C./92% Relative Humidity in % |
| 5 | Polyethylene terephthalate | $Na_3[Al(C_2O_4)_3]$ | 10 | 6.0 |
| 6 | Polyethylene terephthalate | $K_3[Al(C_2O_4)_3]$ | 10 | 9.3 |
| 7 | Polyethylene terephthalate | $K_2][Zn(C_2O_4)_2]$ | 14 | 4.2 |
| 8 | Polyethylene terephthalate | $K_2[Mg(C_2O_4)_2]$ | 20 | 4.3 |
| 9 | Polyethylene terephthalate | $K_4[Zr(C_2O_4)_4]$ | 10 | 4.1 |
| 10 Control | Polyethylene terephthalate | — | | 0.6 |
| 11 | Copolyester of terephthalic acid, 8 mole % adipic acid and ethylene glycol | $K_3[Al(C_2O_4)_3]$ | 10 | 7.9 |
| 12 | Copolyester of terephthalic acid, 8 mole % azelaic acid and ethylene glycol | $K_3[Al(C_2O_4)_3]$ | 10 | 8.9 |
| 13 Control | Copolyester of terephthalic acid, 8 mole % azelaic acid and ethylene glycol | — | | 0.2 |
| 14 | Copolyester of terephthalic acid, 4 mole % isophthalic acid and ethylene glycol | $K_3[Al(C_2O_4)_3]$ | 10 | 8.2 |
| 15 | Polybutylene terephthalate | $K_3[Al(C_2O_4)_3]$ | 10 | 6.2 |

EXAMPLE 16

Undershirts made from Polyethylene Terephthalate (or "PET") with 10% $K_3Al(C_2O_4)_3$ in the polymer mass starting materials and containing half this weight (5%) $K_3Al(C_2O_4)_3$ of the added salts in the finished yarn were compared to similar shirts made of 100% PET, 50% PET/50% (wt.) cotton, and 100% cotton in wear tests conducted in Germany. Two separate tests each utilizing four persons were made. The participants were our colleagues and fellow employees, but were not affiliated with the development of this embodiment of our yarn invention. They were informed that they would be given a single shirt on each of five days, but the five shirts were not all necessarily different. The properties of the shirts and results of testing were:

TABLE 8

| | Property or Result | PET with 10% $K_3Al(C_2O_4)_3$ in Starting Materials | PET | 50% PET/ 50% Cotton | 100% Cotton |
|---|---|---|---|---|---|
| (1) | $K_3Al(C_2O_4)_3$ active portions, amount, % (wt.), total | ~5 | — | — | — |
|  | [Al]% | 0.41 | | | |
|  | [K]% | 1.31 | | | |
| (2) | Weight, g/m² DIN 53-883 | 167 | 182 | 188 | 183 |
| (3) | Air Permeability, l/m² sec DIN 53-887 | 1130 | 1090 | 740 | 540 |
| (4) | H₂O Vapor Permeability, mg/cm² h, DIN 53-333 | 47 | 51 | 50 | 50 |
| (5) | Moisture Regain, % (M.R.) | | | | |

TABLE 8-continued

|   | Property or Result | PET with 10% $K_3Al(C_2O_4)_3$ in Starting Materials | PET | 50% PET/ 50% Cotton | 100% Cotton |
|---|---|---|---|---|---|
|   | (a) 20° C./65% R.H. | 0.8 | 0.1 | 2.8 | 6.2 |
|   | (b) 20° C./92% R.H. | 5.2 | 0.4 | 5.5 | 12.0 |
|   | (c) 34° C./92% R.H. | 5.5 | 0.3 | 4.5 | 10.0 |
| (6) | ΔM.R. | 4.7 | 0.2 | 1.7 | 3.8 |
| (7) | Rate of Wicking, time for 2 mm, DIN 53-924 | >20 min | >20 min | <10 sec | 10 sec |
| (8) | Pore Volume, cc/g |  |  |  |  |
|   | radii < 2.0μ | 0.225 | 0.021 | 0.036 | 0.066 |
|   | radii < 0.75μ | 0.212 | 0.009 | 0.018 | 0.032 |
|   | radii < 150A (See FIG. 8) | 0.086 | 0.007 | 0.003 | 0.018 |
| (9) | Density, g/cc | 1.16 | 1.39 | 1.39/1.52 | 1.52 |
| (10) | Yarn Denier, d/tex DIN 53-812) | 231 | 200 | 190 | 182 |
| (11) | Stitch Density, No./cm |  |  |  |  |
|   | wales (Din 53-883) | 9.6 | 10.0 | 10.6 | 10.2 |
|   | courses (DIN 53-883) | 13.6 | 15.2 | 14.9 | 15.6 |
| (12) | Thickness (2cN/cm²; 25 cm²), mm, Din 53-855 | 1.14 | 1.11 | 1.04 | 1.02 |
| (13) | Pore volume, $\frac{vol}{vol}$, % DIN 53-855 | 89.4 | 88.1 | 87.6 | 88.3 |
| (14) | Water Retentivity (WR), % | 28 | 7 | 23 | 43 |
| (15) | Moisture Perception limit (MPL), hand/apparatus, % R.H. |  |  |  |  |
|   | at 20° C. | 91/>97 | 80/>97 | 86/97 | 80/97 |
|   | at 34° C. | >97/>97 | >97/>97 | 87/>97 | 82/97 |
| (16) | Drying (time from WR to MPL), hand/apparatus, min. |  |  |  |  |
|   | at 20° C./65% R.H. | 23.0 | 21/5 | 35/15 | 39.25 |

The tests were conducted in a room controlled to constant conditions (temperature 19.4°–20.3° C.; R.H. of about 62 to about (66%). Each morning at the same time a participant entered the room wearing underwear (including undershirt), working trousers, working coat, socks, and shoes. Each participant became acclimated to his surroundings by sitting on a chair for about 20 minutes at which time he was asked to remove his coat. He remained seated on the chair for approximately 25 minutes to simulate dry/cold conditions. He then moved to a bicycle ergonometer and worked for about 20 minutes to achieve wet/hot conditions. Following his work, he returned to his seat for about 40 minutes, during which time his body conditions could be termed wet/cold. The test was concluded by repeating the bicycle exercise and cooling periods.

The results of one particular wear test are presented in the following table:

TABLE 9

Wear Tests Under Controlled Climatic Conditions (20° C. 65% Relative Humidity)
With Underwear Made of Hydrophilic PET, PET, PET/Cotton (50/50), and Cotton.
Summarized and Comparative Evaluation of the Wear Hygiene by the Test Persons.

| Test Person | Questions | Did you notice any differences of the wear hygiene at all (moisture and temperature)? | In case of distinct differences regarding wear hygiene (moisture and temperature), please:<br>- state the order (starting with the best fabric)<br>- try to indicate the distance in the order<br>- evaluate the T-shirts by comparing them with what you are accustomed to with your usual underwear. | |
|---|---|---|---|---|
| | | | better than accustomed to | as accustomed to | inferior |
| A | | + | hydrophilic DIOLEN > | cotton = cotton/DIOLEN = Cotton >> | DIOLEN |
| B | | + | hydrophilic DIOLEN ≈ cotton > | cotton/DIOLEN > | DIOLEN = DIOLEN |
| C | | + | hydrophilic DIOLEN > DIOLEN ~ cotton | > cotton/DIOLEN ~ cotton/DIOLEN | |
| D | | + | hydrophilic DIOLEN = hydrophilic DIOLEN | ~ cotton > | cotton/DIOLEN >> DIOLEN |

Explanations:
+ = yes, distinct
o = unclear, since approx. within normal fluctuations
− = no, practically equal
>> = very large difference
> = large difference
~ = hardly any difference
= = no difference N.B.: People commented that hydrophilic DIOLEN (K₃Al(C₂O₄)₃/PET) had better than the normal soil release properties. DIOLEN is a registered trademark of Enka A.G. and related companies, and refers to their PET filaments fibers.

The PET yarn with 10% $K_3Al(C_2O_4)_3$ in the starting materials was seen to perform well in the tests and was given high ratings by each of the four participants. The validity of the test is upheld by the participants' ability to rate identical shirts essentially the same. The tests seem to indicate that 5% moisture regain in our PET yarn with 10% wt. $K_3Al(C_2O_4)_3$ in the yarn is sufficient to achieve comfort properties. As stated earlier, we prefer to achive 7-9% regain in a final product, but the results of the wear test give some flexibility to this desired end property.

We have also attempted to describe the hand of our PET yarn with 10% $K_3Al(C_2O_4)_3$ in the starting materials by asking 12 persons to compare shirts in regard to subjective factors including bulkiness, drapability, warmth, cotton-like appearance, and friction characteristics ("hand"). The test included five shirts, but only two were given to an individual at a time (360 comparisons total). The five shirts were made of (1) the PET yarn with 10% $K_3Al(C_2O_4)_3$ in the starting materials, (2) 100% PET, (3) PET/cotton (50/50), (4) 100% cotton, and (5) PET filament/cotton (80/20). Not only were the participants asked questions concerning drape, warmth, etc., they were asked which of the shirts they preferred in regard only to "hand". The results of the tests were again quite favorable towards our PET yarn with 10% $K_3Al(C_2O_4)_3$ in the starting materials, (1) above. The hydrophilic PET has a warm, rough hand similar to cotton or a 50/50 blend. In overall "hand" preference, shirt (1) was second only to that of the 50/50 blend, with those of 100% cotton, 100% PET sample, and PET filament/cotton (80/20) following in that order.

EXAMPLE 17

Manufacture of Hydrophilic PET yarn with 10% $K_3Al(C_2O_4)_3$ in Starting Materials (Enka A.G., Wuppertal, Germany

A. Preparation of $K_3Al(C_2O_4)_3$ Additive

We have evaluated a variety of synthesis for the production of the $K_3Al(C_2O_4)_3$ additive. Our original preparation was as follows:

$$3KHC_2O_4 + Al(OH)_3 \rightarrow K_3Al(C_2O_4)_3 + 3H_3O$$

This preparation, however, resulted in an undesirable quantity of the dioxalate, $KAl(C_2O_4)_2$, which is not separable from $K_3Al(C_2O_4)_3$. The presence of the dioxalate in our early polycondensation tests resulted in a rapid increase in melt viscosity of the polymer, possibly through crosslinking of the polymer chains. For this reason, a second synthesis was evaluated utilizing potassium aluminate, oxalic acid, and potassium hydroxide in an aqueous medium:

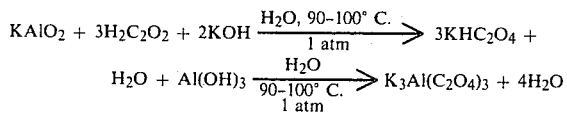

If inexpensive potassium aluminate were employed (as opposed to pure), this synthesis was found unsatisfactory due to impurities in the end product which were not easily separable from the desired product.

We presently produce the $K_3Al(C_2O_4)_3$ additive in a two step process. The first step involves the dissolving of aluminum hydroxide in water in the presence of potassium hydroxide. The species in the solution is $KAl(OH)_4$. This solution is mixed with an oxalic acid solution in the second step of the process to form $K_3Al(C_2O_4)_3$. The entire synthesis may be represented as follows:

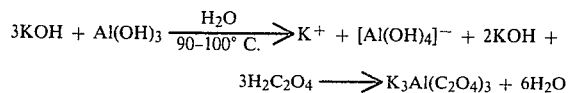

$$3H_2C_2O_4 \longrightarrow K_3Al(C_2O_4)_3 + 6H_2O$$

We have pilot plant facilities to produce $K_3Al(C_2O_4)_3$ in 150 kg and smaller batches. The reaction solution is added to methanol, while stirring, to precipitate the oxalato complex; by products are filtered out, and the oxalato complex may be separated from the methanol/water solution by centrifugation. Two batches may be produced in an 8 hour day. The small pilot plant has glass reactors and a suction filter for recovery of the product. The 150 kg pilot plant has primarily glass-lined vessels which are heated with steam. The vessel in which the $Al(OH)_3/KOH$ solution is made is coated with an epoxy-resin resistant to extreme alkaline conditions. Connecting pipes are made of stainless steel and pumps were obtained locally. It is to be noted that the 150 kg pilot plant was assembled primarily with equipment already in existence at our research facility at Obernburg, Germany, and that composition of the vessels, pipes, and pumps was probably not critical except in the case of the KOH vessel (the corrosive effect of oxalic acid on stainless steel, however, has at this date not been studied in any detail).

Subsequent discussion of the pilot plant will refer to the 150 kg equipment except in instances designated otherwise.

A typical pilot plant preparation of L-75 is conducted in the following manner and shown in FIG. 1: per batch 180 kg of deionized water 1 is first added to an 800 liter stainless steel (or glass-lined, preferably) vessel 2 equipped with a stirrer, and heated to approximately 75° C.-76° C. Over a period of about 30 min., 150 kg of oxalic acid ($H_2C_2O_4.H_2O$; 99.5% pure from Koepp, Oestrich-Winkel, Germany) 3 are added with stirring 4 to the vessel. An additional 10 kg of $H_2O$ from the same source 1 are added for rinsing and the vessel is stirred and heated to about 70°-80° C. for approximately 2 hours. The resulting solution is 44.1% by weight oxalic acid and the density at 70° C. is 1.128 kg/l. The total volume is about 301 liters and weighs about 340 kg. We actually prepare enough for 3 batches at one time for economy.

In a nitrogen-blanketed 1100 liter second vessel 6 (epoxy-coated; alkali resistant), for each batch 34 kg of deionized water 7 (under a nitrogen blanket 8) are added at room temperature. During a 30 minute period, 77 kg of KOH 9 is slowly added with stirring to the vessel. As the KOH (Tablets-Stock 06009, Riedelde Haen, Seelze-Hannover, Germany, theory 67.9% K content, actually 61.4-63.5% K (91.2% pure)) is added from a polypropylene 200 liter vessel, the temperature of the solution begins to rise, and additional heat is slowly added to raise the temperature of the poly-coated vessel to 100°-110° C. About 33 kg of $Al(OH)_3$ (Stock S 65/40, Gebr. Giulini-Chemie, Ludwigshafen, Germany, theory 34.6% Al (based on 100% $Al(OH)_3$), actually 33.4– 34.2% Al (98.8% pure)) 11 are then added over a 15 min. period and the resulting mixture is treated for 20-30 minutes at about 100° to about 110° C.

An additional 96 kg of $H_2O$ 7 are added and stirred until complete dissolution of the $Al(OH)_3$ has occurred. The resulting solution (about 240 kg) is 20.4% K and 4.7% Al and has a density at 29° C. of 1.333 kg/l. Some solution (12 kg) is left over. Actually, enough material for five batches is made.

From pump 12 228 kg of the $KOH/Al(OH)_3$ solution is pumped to a volumetric polypropylene holding tank 10 and for each batch 340 kg of the oxalic acid solution is transferred to a 500 liter glass-lined autoclave 14 (note that much simpler equipment than an autoclave may be employed). The autoclave 14 is available from Pfauder-Werke A.G., Post Box 87, D6830 Schwetzingen, Germany. The pump 5 transferring the acid solution is heated with steam to prevent recrystallization of the solid and subsequent pump blockage; however, we believe that if proper configuration of the connecting pipes is utilized, a heated pump 5 is not necessary. The $KOH/Al(OH)_3$ solution is slowly added at 103°–105° C. to the autoclave 14 with good stirring until a pH of 4.00–4.05 is reached, using additional $KOH/Al(OH)_3$ from vessel 10 if needed. The resulting solution is held at 100°–105° C. for about ¼ hour and is then transferred to another 1100 liter vessel 15 for cooling. As the solution cools after 2 hours to about 20° C., any impurities including the dioxalate ($KAl(C_2O_4)_2$) and unreacted $Al(OH)_3$ precipitate. Usually little or no precipitate is obtained, and we now believe that complete cooling may not be totally necessary. The charge (568 kg, ~480 l) is transferred by pump 16 through a cotton cartridge-type filter 17 (Scheibler Co., Germany, 10μ rating) to a 1300 liter vessel 18 (or vessels (or vessels 18a and 18b) containing 440 l-460 l of methanol in two stages at 15°-20° C. (a 1:1 ratio by volume is thought to be optimal—too little methanol results in poor separation; too much methanol results in uneconomical operation). In the first stage, one half of the charge is added to 220 l methanol which is <15° C.; the second stage is a repeat. The filter may be thrown away after about 10 batches. The discarded filter will contain predominately undissolved aluminum hydroxide and some dioxalate. The methanol is obtained from a DMT-based polymerization process and utilized without any further purification. The mixture is stirred 19 at less than about 30° C.-34° C. for about 20 min. to insure complete precipitation of the $K_3Al(C_2O_4)_3$ complex, and methanol makeup from tank 21 added if necessary. Approximately 120 l of the mixture are then transferred by gravity to a centrifuge 20 (Model GZ 850, 850 mm diameter, Carl Padberg, Lahr/Bohn, Germany) where it is processed for 25 min, at 1500 rpm. The process is repeated for eight times at about 115 kg each until the entire autoclave batch has been recovered. A continuous centrifuge (Schälzentrifuge, Model HZ 80, Kraus Maffei, Germany) is recommended. There is from about 11–15% $H_2O$ residual moisture in the filter cake. No problems are encountered in transporting the precipitate/methanol/water mixture if the particle size of the complex is reasonably small. The methanol/water effluent 22 (approximately 50:50 by weight with 1.0–1.5% complex) is distilled in 1000 l batches which take about 8 hours to recover the methanol; the remaining water, 23, 23a containing about 1% residual oxalato complex is discarded 24 after filtration. The wet $K_3Al(C_2O_4)_3$ is sent to a dryer 25. Vapor 27 is condensed in condenser 28 for recycle.

The $K_3Al(C_2O_4)_3$ from the centrifuging process includes three moles water and has a specific gravity of about 2.0 and a water content of about 5.0% to about 15.0%. The three moles of water are lost at 60°, 90°, and 130° C. respectively. The more effective the centrifuging step is, the less time is required for drying.

A variety of dryers has been evaluated for use in the pilot plant. Vacuum ovens have been utilized for small scale batches, but are ineffective for larger scale work. Dust comprising $K_3Al(C_2O_4)_3$ can also be a problem when vacuum ovens are employed. Extreme heat is to be avoided as $K_3Al(C_2O_4)_3$ decomposes at 440° C. We believe the most efficient dryer to be a Drais Company (Mannheim, Germany) rotary type with intermeshing blades which are capable of scraping the walls of the vessel. Under conditions of 220° C. and 30 mm pressure, an 80 kg batch of $K_3Al(C_2O_4)_3$ was dried in the vessel from 11% $H_2O$ to about 0.4–0.5% $H_2O$ in 30 min. and to about 0.1% in one hour product 26. Originally, we heated the cake at 170° C. for about 16 hours to obtain a residual moisture of less than about 0.1%. Paper filters (<5μ) and a condenser are inserted in the vacuum line to catch dust and water, respectively. The powder is hygroscopic.

Few quality control checks are needed on either raw materials or the finished $K_3Al(C_2O_4)_3$ product. Titration techniques are used to determine the purity of KOH and oxalic acid, and X-ray fluorescence is employed to determine the amount of Al in $Al(OH)_3$. Presently the $K_3Al(C_2O_4)_3$ additive is not analyzed for impurities prior to use in polymerization. If an abnormal increase in melt viscosity is noted during polycondensation, samples of the additive are analyzed for dioxalate content. The dioxalate exhibits an infrared absorption at 1050 cm$^-$, while $K_3Al(C_2O_4)_3$ does not.

B. Dispersion of $K_3Al(C_2O_4)_3$ in Glycol $K_3Al(C_2O_4)_3$ is presently added to polymerization process in the form of a 30% dispersion by weight in glycol, although a range of 28%–30% by weight is found to be acceptable. The object of the content of the $K_3Al(C_2O_4)_3$ in the dispersion is to obtain an approximate 10% by weight oxalato complex active-portion content in the finished yarn. The dispersion is prepared with a Pentax (Pentax Co., Model MFR 200, Kassel, Germany premixer and a series of pearlmills (sandmills)). During the premix process, the particle size of the additive is reduced from about 200μ to about 10μ. No dispersent is needed. The smaller plant employs a series of four pearlmills and three filters in the following way to prepare the dispersion.

Figure 2:
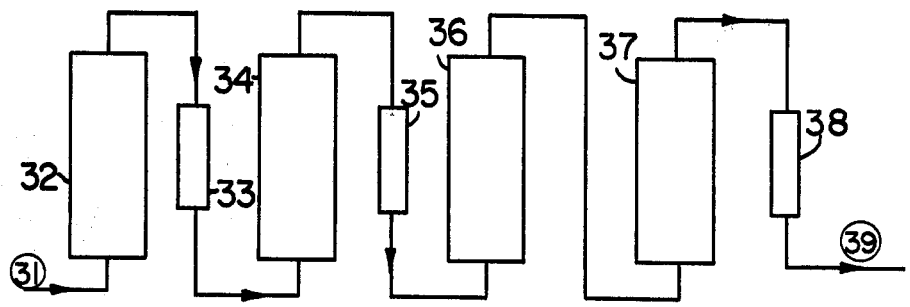
FIG. 2 is an overall schematic flow diagram of a series of pearlmills and filters used in a small pilot plant for the preparation of a suspension containing $K_3Al(C_2O_4)_3$.

In FIG. 2, premix 31 is sent to pearlmill 32 (3 mm) and thereafter the dispersion flows through 10 filter 33 to 2 mm pearlmill 34. Afterward, the dispersion is again filtered through 5μ filter 35 before passage to 1 mm pearlmill 36 and final 0.75 mm pearlmill 37. The finished product is filtered by a 3μ filter 38 and sent to storage 39 (not shown). The pearlmills have a volume of 5 liter each and are operated at a speed of 1 kg/hr/l. Normal siliquarzit-type pearls (SQP type) are employed and recommended, and no problems have been encountered thus far with abrasion of the equipment. $Al_2O_3$ pearls yielded a gray dispersion. Siliquarzit pearls from the Drais Co., Mannheim, Germany are recommended. Cotton cartridge-type filters are employed and pressure buildup was found not to be excessive. The 3μ filter is normally changed after 3 days, but longer running times are possible. The dispersion leaving the 3μ filter has an average particle size of 0.5 to 1.0μ and almost never contains particles >2μ. Settling of the suspension is not recommended, and the slurry is stable for up to about 4 weeks.

Due to mechanical problems in the dispersing equipment of the 150 kg pilot plant, all $K_3Al(C_2O_4)_3$ suspensions added to plant polymerizations have been produced in the pearlmills of the smaller pilot plant. The dispersing equipment of the larger pilot plant is represented in FIG. 3.

Figure 3:
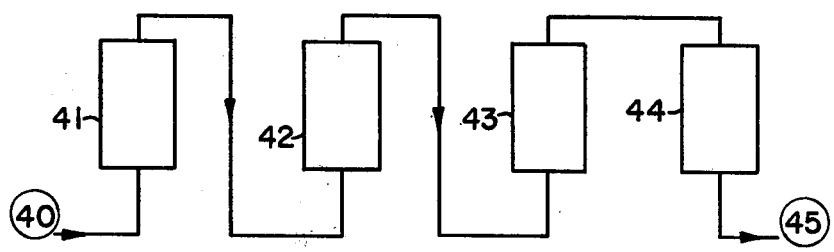
FIG. 3 is an overall schematic flow diagram of a series of pearlmills and filter used in a larger pilot plant for the preparation of a suspension containing $K_3Al(C_2O_4)_3$.

In FIG. 3, premix dispersion 40 is sent through three pearlmills 41, 42, 43 (3 mm, 2 mm, 1 mm, respectively) before being filtered in $3\mu$ filter 44 and shipped to storage 45 (not shown).

The pearlmills are operated at a speed of 1 kg/hr/l. A fourth mill with 0.75 mm pearls may be added to the system if needed; and additional filters between the mills will also be added if they are determined to be necessary.

Suspensions may be shipped for polymerization (if the process for manufacture of the suspension is in a different location than polymerization and drying) in aluminum cans with polypropylene liners. Although shipping may take place under a nitrogen blanket, such may not be necessary. The suspension becomes gray if it comes in direct contact with aluminum. The cause for the increase in grayness has not been determined.

C. Polymerization and Drying

1. Ester Interchange (EI)

Figure 6:
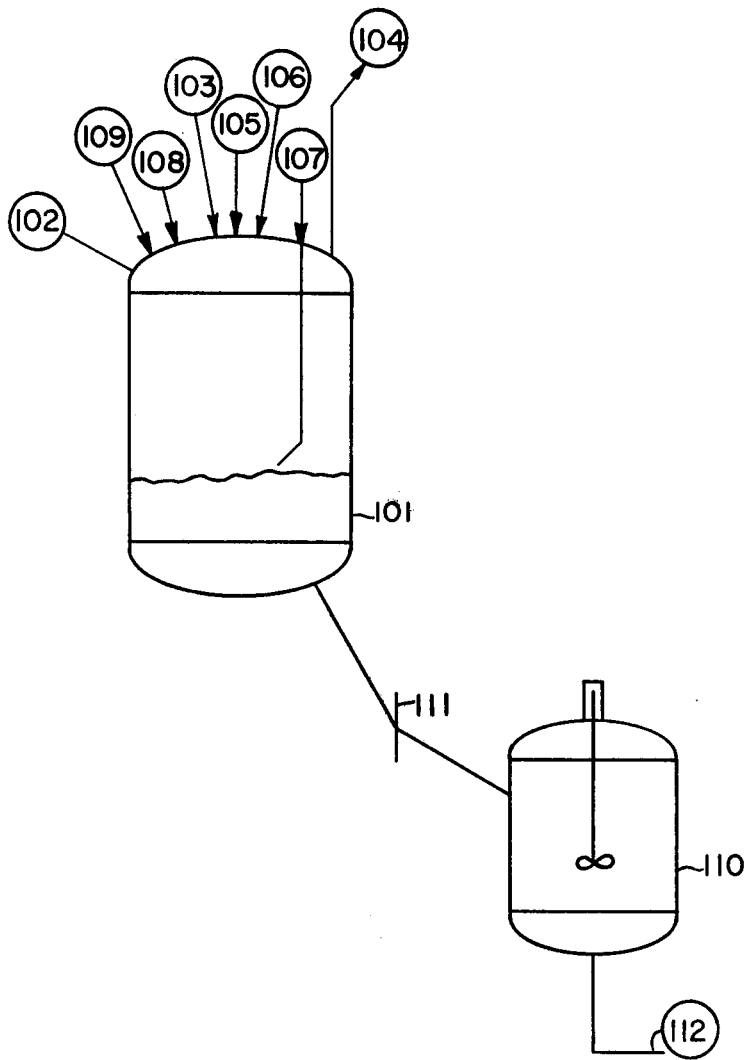
FIG. 6 is an overall schematic flow diagram of the polymerization steps and addition of $K_3Al(C_2O_4)_3$ for the manufacture of chips containing 10% $K_3Al(C_2O_4)_3$ in the starting PET materials, prior to drying of the chips.

Referring to FIG. 6, our pilot plant operation employs a large heated stainless steel vessel 101, to which glycol 102 and dimethyl terepthalate 103 are first added in stoichiometrically predetermined amounts at 150° C. The temperature of the mixture gradually climbs over at least about 90 minutes to 220°-230° C. in which time methanol 104 is distilled off at a temperature from 180° C. to 220° C. The reactor is kept under a nitrogen blanket at slightly above atmospheric pressure (0.7 bar). The reaction mixture is then stirred for about 25-30 minutes, in which time an effective phosphoric acid stabilizer 105 is added. Antifoamer (supra) 106 is also added. Five minutes later, we then add the 30% $K_3Al(C_2O_4)_3$/70% ethylene glycol suspension 107 to the ester interchange process at a temperature of 220°-230° C. Addition time for the slurry is 10-15 min., and the feed rate is controlled by a hand valve to prevent significant decreases in melt temperature. The ester interchange (EI) vessel was chosen as the point of addition for the suspension because of the much higher stirrer speed during the process as opposed to the stirrer speed in our autoclave 110 (AC). The $K_3Al(C_2O_4)_3$, however, reacts with EI catalysts to inactivate them, and thus addition of the suspension must follow completion of any methanol cycle. Furthermore, residual $K_3Al(C_2O_4)_3$, which adheres to the walls and heating coils of the vessel, is capable of poisoning the catalyst in subsequent batches. Several possible solutions to this problem are taught as follows:

(1) Use the two conventional vessels but clean the ester interchange reactor after every batch. We consider this to be the simplest solution and recommend equipment made by Kärcher (Leutenbacherstrasse 30, 7057 Winneden, Württ, Germany). The Kärcher equipment extends into the center of the ester interchange vessel and clean with glycol under pressure through a rotating head. Glycol distilled from the EI process may be employed in the cleaning equipment. Any glycol used in cleaning will probably be sent to the AC, although it is probably less expensive to process the glycol in its recovery unit.

(2) Add an additional vessel for mixing between the ester interchange and the autoclave. If possible, this vessel should be used to distill the excess glycol added with the $K_3Al(C_2O_4)_3$ additive and to conduct the initial portion of polycondensation;

(3) Add $K_3Al(C_2O_4)_3$ to the autoclave; and (4) Incorporate $K_3Al(C_2O_4)_3$ into the polymer during spinning, preferably using a twin-screw extruder.

Polymerizations containing $K_3Al(C_2O_4)_3$ presently employ calcium (in acetate form) as an ester interchange catalyst. Calcium acetate was chosen, as opposed to Mn or Zn, because quantities as large as 1000 ppm could be added to the reaction without undesirable effects. Approximately 0.5 ppm of a solution consisting of 10% by weight BAYSILON EN ® (Bayer A. G., Leverkusen, Germany) antifoamer in water is also added.

The methanol cycle for the process is normal with the exception that calcium is used. At the end of the methanol cycle, the phosphoric acid stabilizer is added, and five minutes later at 220° C. the addition of the $K_3Al(C_2O_4)_3$ begins. Addition is through a 25 mm pipe 107 which extends to the center of the vessel and stops 20 cm above the liquid level. Heating of the melt was continued and atmospheric glycol distillation is accomplished. No vacuum glycol distillation was employed for any of the polymers. Addition of 500-600 ppm UVI-TEX 551 ® (Ciba-Geigy, Basel, Switzerland) optical brightener 108 is performed at about 240° C., and five minutes later 400 ppm of $Sb_2O_3$ 109 (Electrochemie, Ibbenbüren, Germany) is added. The final EI bottoms temperature is 255° C. The addition of $K_3Al(C_2O_4)_3$ increases the EI cycle time by 30-45 minutes.

Normally, the PET ester interchange product is filtered with two screens in series; however, for the $K_3Al(C_2O_4)_3$ polymer, the two screens have been replaced with a single 40 filter 111. We have, at this time, not had enough experience with the $K_3Al(C_2O_4)_3$ polymer to predict filter life, but large amounts of debris are deposited on the filter during transfer of the monomer. Pressure (2.5 bar) from gravity is employed in transferring the ester interchange product (about 255° C.) to the autoclave. The ester interchange vessel may be cleaned as often as necessary by an INNENREINIGER HFK 200 ® cleaner available from Alfred Kärcher, Leutenbacherstrasse 30, 7057 Winnenden/Württ, Germany.

2. Polycondensation

During polycondensation, the melt viscosity of the $K_3Al(C_2O_4)_3$ polymer is approximately twice that of normal. The abnormal viscosity has caused several changes in standard polymerization procedures. Batch size was reduced about 22% to improve stirring. The reduced batch size also decreases the autoclave 110 cycle time so that autoclave and ester interchange times are better balanced. In FIG. 6, the autoclave 110 of our pilot plant is stainless steel. Autoclave stirrer speeds had to be reduced from 26/13 rpm to 26/6 rpm to prevent the polymer from climbing the stirrer shaft.

We found that polycondensation temperature at 280° C. to be optimal. Pilot plant polymerization conducted at 290° C. resulted in undesirable color and degradation during extrusion. However, a peak heating method may be possible if rapid cooling from 290° to 280° C. occurs before extrusion. We have found that cycle time at 280°

C. for the $K_3Al(C_2O_4)_3$ batch is slightly longer than the normal batch (22% larger) processed under standard conditions.

For normal PET operations, we extrude a PET ribbon 112 2.5 mm thick under 5 bar pressure. However, utilization of the normal extrusion die with $K_3Al(C_2O_4)_3$-containing PET polymer results in a ribbon 1.5 mm thick, and 7 bar pressure must be employed to empty the AC in a reasonable length of time. Therefore, a special extrusion die was designed which allows an $K_3Al(C_2O_4)_3$-containing ribbon with normal thickness to be extruded under 5 bar pressure. The ribbon (having 0.3% water content) is more brittle than normal PET, and fast extrusion is not necessary. At 280° C., the solution viscosity of the polymer drops from 1.66 to 1.62 during a 35 minute extrusion. Due to the hydrophilic nature of the ribbon, hot air (185° C.) is blown across the polymer before chipping to remove excess water. After chipping, the polymer is analyzed for intrinsic viscosity (the procedure takes into consideration that 10% of an inert material is present), softening point (usually ~263°-264° C.), potassium and aluminum content via X-ray fluoroscence, color, carboxylic end groups (28-29 meq/kg), and % DEG (ca. 1.1%). Water content is about 0.1% by weight.

3. Drying of Chips

Figure 4:
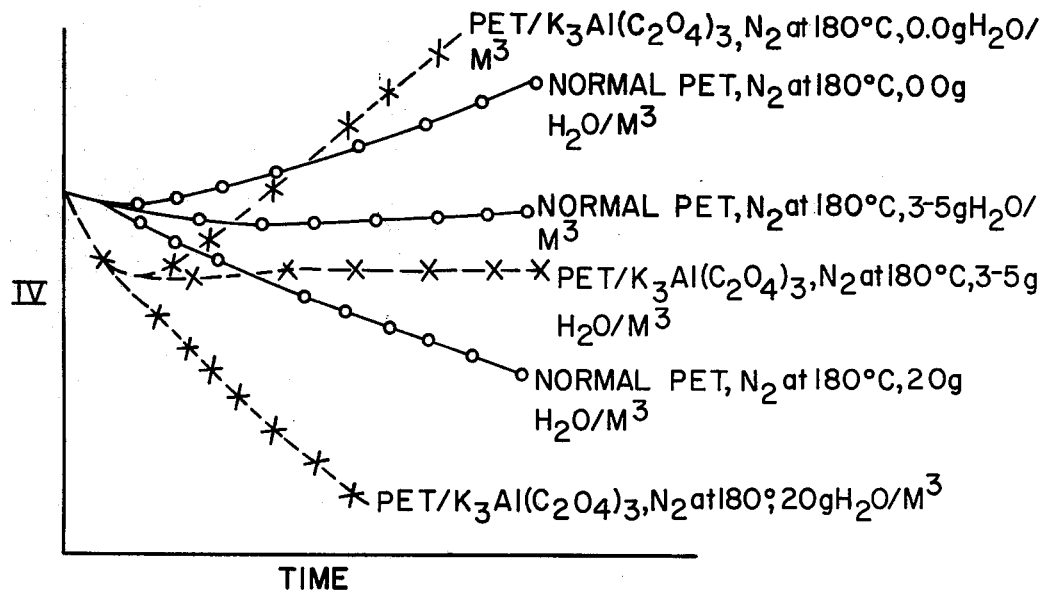
FIG. 4 is a graph plotting the general function of intrinsic viscosity against time comparing viscosity changes of normal PET and PET with $K_3Al(C_2O_4)_3$ in the drying of chips.

When compared to normal PET, we have $K_3Al(C_2O_4)_3$ polymer to be more susceptible to hydrolytic degradation during drying and it is also probably more sensitive to hot air. Viscosity decreases may be overcome by the polymer's increased tendency to postcondense as shown by the general chacteristics of FIG. 4. The $K_3Al(C_2O_4)_3$/PET polymer picks up moisture during casting which eventually penetrates to the center of the chips and results in an intrinsic viscosity (IV) drop during the initial period of drying. Attempts are made to remove excess water during casting by blowing air over the ribbon before chipping. Before filament spinning, the chips are placed in tumble dryer at 120° C. under vacuum for 3-4 hours. An IV drop of 0.1 occurs as the chips dry to 0.02% $H_2O$. After this pre-drying step, we have found the chips may be stored for periods of several months without subsequent spinning problems.

Just prior to spinning, final drying is accomplished in a normal batch rotary dryer known to those skilled in the art at 150° C. under vacuum (1 or 2 mm Hg) for 6 hours. The final $H_2O$ content is about 0.006%, and the solution viscosity about 1.65. Under these conditions, some postcondensation occurs, and the final IV of the polymer is about that of the undried chips. The chips can be stored in a nitrogen blanket from about 2-3 months to about 1 year without significant degradation.

Due to the brittleness of the polymer, the dust level in $K_3Al(C_2O_4)_3$/PET chips is considerably higher than in normal PET. Since the dust tends to postcondense more than the chips, we originally removed the dust by sieving. Presently, however, the dust need not be removed, and the IV is controlled by drying times and temperatures.

We have found that in transporting $K_3Al(C_2O_4)_3$/PET chips in pipelines, a larger percentage of chips cling to the interior of the pipe than do normal PET chips, possibly because of static problems.

D. Spinning and Drawing

1. Filament Spinning $K_3Al(C_2O_4)_3$ polymer with a solution viscosity of 1.59 is comparative in rheological properties to normal PET with a solution viscosity of 1.69. We have found that a 25° C. increase in temperature is needed to get the same flow behavior with L-75 polymer as with normal PET. The higher melt viscosity of the polymer may be overcome by a 10° C. increase in spinnerette temperature (290° C.) and utilization of spinnerets with a hole diameter of 350μ instead of 250μ.

A test method was developed for evaluating the spinnability of $K_3Al(C_2O_4)_3$ polymer samples. A spin pack is constructed with 15 screens of 16,800 mesh/cm$^2$ alternating with 15 screens of 1,600 mesh/cm$^2$. The test is conducted until the melt pressure in front of the spinneret pack reaches 250 bar. Originally spinning times as low as 8-10 hrs. were attained with the test method, but with normal adjustments, additive dispersion (within the skill of one in the art) will increase the running times to 72 hours. We think that a spinning time of 2-3 days indicates an acceptable polymer quality.

Filtration during filament spinning of $K_3Al(C_2O_3)_3$/PET polymer is accomplished with a 20μ Panzer (Metalltuchfabrik, Düren, Germany) screen as a central product filter and a spin pack composed of 20 screens of 6400 mesh/cm$^2$ alternating with 20 screens of 1600 mesh/cm$^2$. Using such a filtration system, running times of 100-120 hours may be attained before the melt pressure reaches 250 bars, and the spinneret has to be changed. Particle size and gel formation and two factors affecting filtration and running time. Using spinnerets with 350μ holes, we have successfully spun PET polymer containing 10% by weight $K_3Al(C_2O_4)_3$ into dtex 76/f24 yarn at 1200, 2000, and 3500 meters per minute (mpm). When 250μ holes are employed, only speeds of 1200 and 2000 mpm have been attained. Scraping of the spinnerets is required every 12-24 hours with the 350μ holes and every 3-4 hours with the 250μ holes. Acceptable break levels during drawtwisting may be obtained using the same conditions as for normal PET.

Immediately before hydrosetting, the dry drawn yarn exhibits the following properties:

TABLE 10

| | |
|---|---|
| Density | 1.25-1.28 |
| Pore Size | 50 Å to 2μ |
| Pore Volume | 0.10 cm$^3$/g |
| Moisture Regain, Absolute | 7% at 92% R.H. and 40° C. |

It is significant to note that the density of the yarn decreases from 1.38 before drawing to about 1.25-1.28 after drawing.

2. Staple Spinning

In one trial, $K_3Al(C_2O_4)_3$/PET polymer was spun with staple spinnerets. The longest staple spinning trial was for 10-12 hrs (400 kg polymer tested), and 1.7 dtex staple was produced. Scraping of the spinnerets was not required during the trial, and no filament break problems were experienced. The spinneret for the trial had 769 holes with a hole diameter of 300μ. The spinneret hole configuration employed an offset grid, e.g., a square formed between any four holes, one in a first row, two in the second row, and one in a third row; the distance between the centers of adjacent holes in the spinneret was 6.5 mm. Melt temperature was maintained at about 290° C., while the spinneret was controlled at about 286° C. Take-up speed was 1365 mpm. If 3.0 dtex staple is desired, a spinneret of 571 holes with hole diameter of 300μ is employed. A series of 20 screens with the following mesh/cm² ratings were employed as a filtration media:

TABLE 11

| Screens | mesh/cm² |
|---|---|
| (1) | 625 |
| (2) | 16,800 |
| (3)–(4) | 2 × 1000 |
| (5)–(6) | 2 × 625 |
| (7) | 16,800 |
| (8) | 625 |
| (9)–(10) | 2 × 3000 |
| (11) | 625 |
| (12)–(13) | 2 × 1000 |
| (14) | 625 |
| (15)–(16) | 2 × 3000 |
| (17) | 625 |
| (18)–(19) | 2 × 1000 |
| (20) | 625 |

The batch hydrofixated (see infra) staple fiber had the following characteristics:

| | |
|---|---|
| Fiber | 1.7 dtex |
| Fiber Length | 40 mm |
| Tenacity | 36 cN/tex |
| Elongation | 38% |
| Crimp | 16% |
| Number of Half Crimps (Waves/100mm) | 100 |
| Shrinkage: | |
| In water at 125° C. | 2% |
| in hot air at 190° C. | 5% |
| Water Retention Power | 30% |
| Moisture Absorption: | |
| 22° C./65% R.H. | 2% |
| 34° C./92% R.H. | 7% |

Presently, a two-step drawing process is employed with an overall draw ratio of 1:3:8. The temperature of the first five rolls in the first septet is 70° C. and the last two rolls are controlled at 110° C. The second septet is operated at room temperature. Approximately 80% of the drawing is conducted in the first zone, and 20% in the last step. The drawn tow exhibits the following properties before hydroheatsetting:

TABLE 12

| | |
|---|---|
| density | about 1.4 g/cm³ |
| fineness | 1.6 |
| elongation | 28–30% |
| tenacity | 35–37 cN/tex |
| hot air shrinkage, 190° C. | 18% |

See also Table 1.

3. Spin Finishes

We have come to the conclusion that the following finishing steps are the best. With spinning, the usual PET preparation is used. It contains a neutralized phosphoric acid as an antistatic material (e.g., ARDUE M423 TM, Akzo-Chemie, Düren, Germany) in mixture with an emulsifying agent of the fatty alcohol-ethoxylate type (e.g., GENAPOL GX 050 TM, Hoescht A. G., Frankfurt, Germany). The preferred mixture is from about 50/50 to about 90/10 by weight. This preparation is also present in the emulsifying bath before drawing. The application amount taken up is preferably from 0.1 to about 0.3 weight percent.

After the hydrofixation, the preparation is present on the surface of the filament in an essentially non-active concentration. Before crimping, a combination of an emulsified and non-modified silicon oil (e.g., PERSOFTAL NG TM, Bayer A. G., 5090 Leverkusen, Germany) in combination with a modified silicon oil (e.g., L7602, Union Carbide Co., New York, New York, U.S.A.) in the preferred mixing range from 10/1 to 2/1 and in a preferred total amount from about 0.4 to about 0.6% is applied, using a bath. Additionally, shortly before textile spinning, a very active antistatic agent (e.g., HOET 2561 TM, Hoechst A. G., Frankfurt, Germany, or Hoechst, Somerville, N.J.) is sprayed on in the preferred amount of 0.2 to about 0.4% by weight.

E. Hydroheatsetting

1. Discontinuous vs. Continuous Processing

Although the hydroheatsetting (HHS) process is essential in the production of $K_3Al(C_2O_4)_3$/PET yarn, much is still not understood about its function. Drawn $K_3Al(C_2O_4)_3$/PET yarn may not be exposed before HHS to temperatures greater than about 120° C. However, if the drawn yarn is not exposed to high temperature before HHS, the additive is found to be stable against fifty commercial washings at 25° C.–40° C., each for 10 min.–30 min. Furthermore, we have found that heat treatments after HHS have virtually no effect on $K_3Al(C_2O_4)_3$ yarn.

For discontinuous hydrosetting, we have found that liquid water in excess of 30% of the weight of the textile should be present in HHS for an effective process, and more than 100% of the weight of the textile. For both continuous and discontinuous hydrosetting, saturated steam by itself has the same effect as a hot air treatment (loss of additive during subsequent washing). Steam may be used, however, in conjunction with water to obtain a stable hydroheatset yarn.

Originally, we employed a commercial high temperature (HT) dye machine to hydroheatset $K_3Al(C_2O_4)_3$/PET in staple form in a discontinuous process. The cycle time for the process may be outlined as follows:

30 min. to reach 135° C.
10 min. at 135° C. for HHS
20 min. to cool to 95° C.
10 min. rinsing at 40° C.

During the discontinuous process (1 hour hydroheatset treatment in water at 125° C.), shrinkage levels as high as 30% were obtained in the staple, although most trials had 15% shrinkage. The roughness of the fibers hydroset in the autoclave and the high shrinkage causes the staple to tangle or to mat, and the individual fibers had to be separated by hand before further processing into yarn. Fibers could not be opened easily and cord loading resulted, although after the fiber was dyed and finished, about 8% by weight $K_3Al(C_2O_4)_3$ remained in the fiber, and about 5% after 50 home launderings at 25° C.–40° C. The rough surface with its breaks and oligomer deposits caused by the long hydrosetting times were the cause of many mechanical problems in secondary spinning. This led us to try continuous hydrofixation, which avoids the high energy cost and limited quantity availability of discontinuous hydrofixation. The following Table summarizes comparative testing between discontinuous and continuous methods using a PET polymer with 10% $K_3Al(C_2O_4)_3$:

TABLE 13

|  | Shrinkage of Final Yarn | Tensile Strength | Elongation |
|---|---|---|---|
| I. Normal Aftertreatment | | | |
| TYPE 12 heatset | 6% | 38cN/tex | 22% |
| TYPE 11 non-heatset (200° C. septet) | 20% | 36cN/tex | 22% |
| II. Drawing Aftertreatment Only (no hydroheatset, no elevated temperature, drawing at 180° C.) | 35% | 39cN/tex | 25% |
| III. Batch Hydrofixation (125° C., 1 hr., water) Moisture Regain: 8.5% | 5% | 28cN | 45% |
| IV. Continuous Hydrofixation (25 m/min. in a Serracant (Sabadell, Spain) tube; about 135° C.) Moisture Regain: 7.4% | 2% | 28cN/tex | 44% |

The problems encountered with the discontinuous process have caused us to search for a means of continuously hydroheatsetting $K_3Al(C_2O_4)_3$/PET in tow form.

Figure 5:
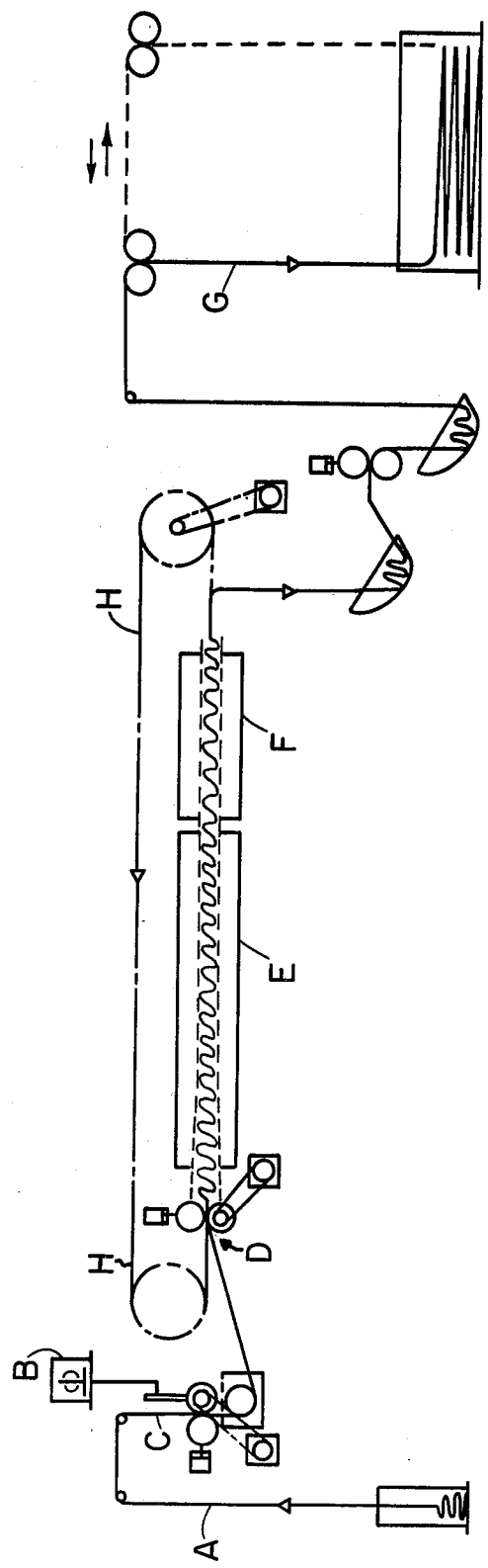
FIG. 5 is a overall schematic flow diagram of a Serracant (Sabadell, Spain) machine to be used for continuous hydrosetting of PET with $K_3Al(C_2O_4)_3$.

An experiment was made under the usual conditions with conventional equipment for tow for heatsetting and dyeing, produced by Serracant of Sabadell, Spain. A flow diagram is given in FIG. 5.

In practicing this experiment, 140 kg of drawn tow of 46.6 ktex (single filament: 1.7 dtex) of PET with 10% $K_3Al(C_2O_4)_3$ in the polymer mass starting materials was fed from entrance zone A to a foulard C and freed from air. Foulard C was supplied water from water tank B. The tow was then wetted to 90% (relative to dry conditions) with water of 20° C. Then in a fixating zone E the tow was heated with saturated steam to each of 130° C./139° C./133° C. in the separate trials, and afterwards washed in a washing zone F with 40° C./30° C./20° C., respectively. The speed of winding from transport chain H constituted the first part of the experiment, and in one trial was 25 m/min., so that the residence time of the tow in the Serracant device was 6 min., 45 seconds, and in the second trial was 40 m/min., with a residence time of 4 minutes. The heatset tow passed to storage G.

In the trial of 25 m/minute, no troubles developed. With 40 m/minute, after a short time there were troubles caused by unsatisfactory tow build-up (provisional assembly of a lot of bent ribbon crimped, tow transported wide distances). Experiments with higher speeds and respectively shorter residence times could not be made.

The results are given in Tables 14 and 15, where there are given pertinent data before and after the hydrofixation, and some values concerning the pore system before and after hydrofixation and until finishing.

TABLE 14

| Textile Data | Untreated | Serracant-hydrofixed 25 m/min. Entrance | Serracant-hydrofixed 40 m/min. Entrance |
|---|---|---|---|
| Fineness, dtex | 1.7 | 2.1 | 2.1 |
| Breaking strength, cN | 6.5 | 5.9 | 5.9 |
| Breaking strength, cN/tex | 39.0 | 28.0 | 28.3 |
| Elongation, % | 25.5 | 44.2 | 46.9 |
| Load at 10% Elongation | 26.8 | 6.7 | 7.0 |
| Flexing Abrasion Resistance, T | 7349 ± 1130 | 2009 ± 307 | 2158 ± 408 |
| Crimp, % | 6.5 | 11.6 | 7.2 |
| No. of half crimp waves/100mm | 89 | 126 | 64 |
| Shrinkage in Boiling Water, % | 23.0 | 0.3 | 0.1 |
| High Temperature Shrinkage (at 125° C.), % | 19.1 | 0.1 | 0.2 |
| Hot Air Shrinkage (at 190° C.), % | 34.9 | 2.2 | 4.0 |

TABLE 15

Results of PET/$K_3Al(C_2O_4)_3$ Yarn After Certain Steps)

| Test | Moisture Regain, % 40° C./92% R.H. | R.F. Analysis (X-Ray Fluoresence) K % | R.F. Analysis (X-Ray Fluoresence) Al % | Pore Volumn With Radius (A), cm$^3$/g <150A | Pore Volumn With Radius (A), cm$^3$/g <7500A | Pore Volumn With Radius (A), cm$^3$/g <20,000A | Density g/cm$^3$ |
|---|---|---|---|---|---|---|---|
| Untreated Yarn | | | | | | | |
| unstretched yarn | | | | | | | |
| stretched yarn | 32 | 2.81 | 0.61 | 0.004 | 0.017 | 0.029 | 1.398 |
| After Hydrofixation (Bath) | 7.0 | 2.14 | 0.55 | 0.106 | 0.192 | 0.202 | 1.177 |
| Serracant treated at 25 m/min | 7.4 | 2.50 | 0.53 | 0.135 | 0.250 | 0.255 | 1.242 |
| Stable Fiber Crimped Tow | 7.9 | 2.16 | 0.54 | 0.106 | 0.140 | 0.147 | 1.244 |
| Cut and Carded | 6.3 | 1.94 | 0.52 | 0.079 | 0.124 | 0.132 | 1.272 |
| Without Steam treatment, Yarn | 5.9 | 1.95 | 0.5 | 0.055 | 0.082 | 0.096 | 1.242 |
| With Steam treatment, Yarn | | | | | | | |
| Raw Material | | | | | | | |
| High Temperature Dyed Yarn | 5.6 | 1.31 | 0.36 | 0.145 | 0.299 | 0.320 | 1.086 |
| End Use | | | | | | | |
| Grey Socks | 5.6 | 1.52 | 0.38 | 0.116 | 0.250 | 0.277 | 1.140 |

F. Textile Finishing

Figure 7:
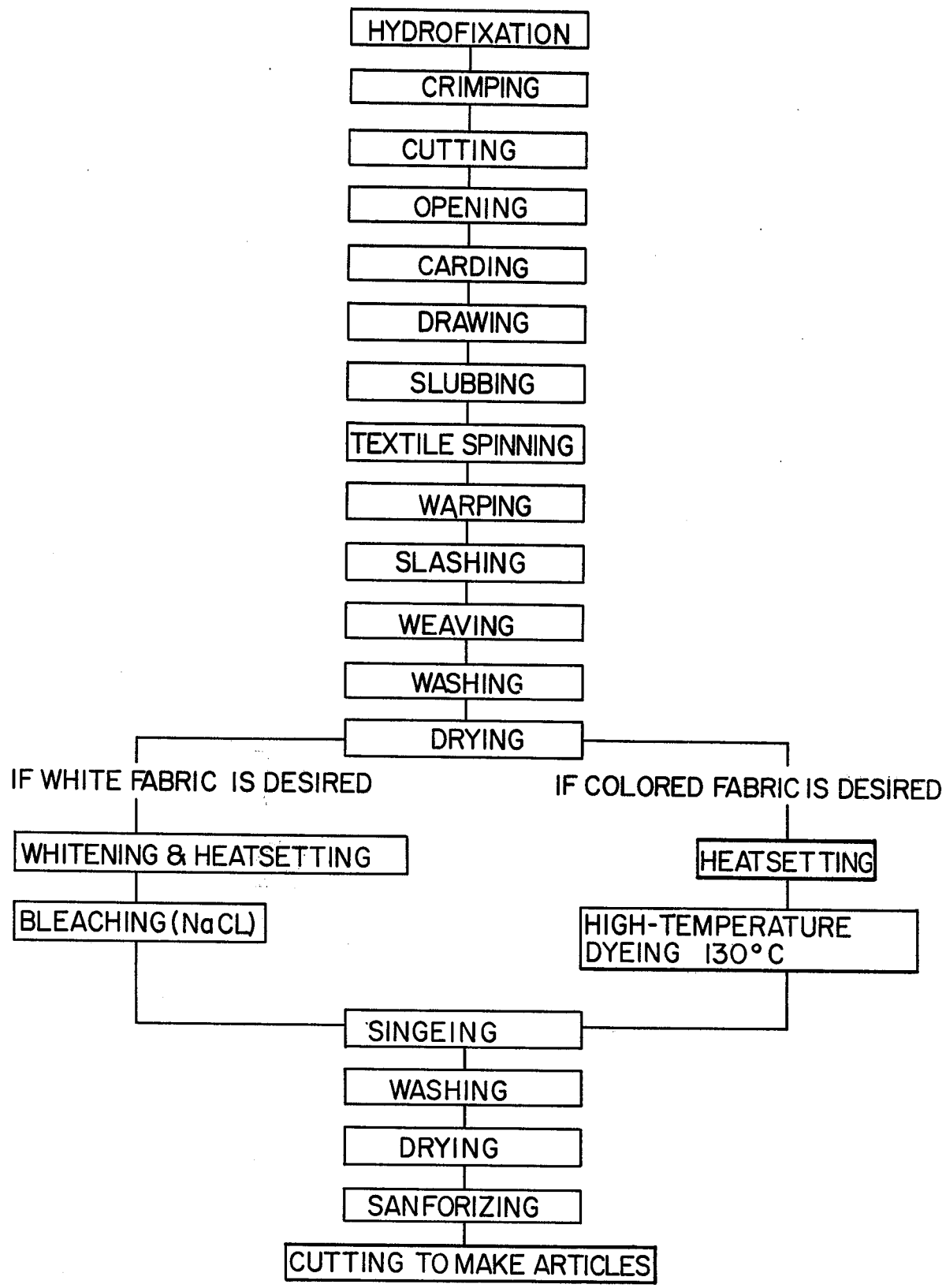
FIG. 7 is one overall block diagram of the various steps subsequent to hydrofixation of yarn containing 10% $K_3Al(C_2O_4)_3$ in the starting PET materials, e.g., the textile finishing steps.

After hydrosetting, the material is crimped and cut in a normal fashion and processed according to steps well known to those in the art (see FIG. 7 with Flow Chart). PET/$K_3Al(C_2O_4)_3$ yarn is subject to dyeing problems (up to 300-400% of normal amounts of dye are needed, especially for dark colors, as compared to normal PET with the same denier per filament), probably due to the existence of the unusual pore system; soil release tests under experimental conditions with carbon black show favorable results. Comparable soil release properties of $K_3Al(C_2O_4)_3$/PET versus normal PET were obtained under wear conditions of Table 9—and under usual conditions—e.g. household washing—in common wear conditions:

TABLE 16

SOIL RELEASE TEST
(1 part textile: 30 parts $H_2O$ and carbon black)

Percent Degree of difference of Reflection: $\left(\dfrac{Rc - Rd}{Rc}\right) \times 100^{**}$, 60° C.

| | Number of Washes at 60° C. | R1: Bleaching With $NaClO_2$ Use Optical Whitener, THERMOSOL® Hot Air 30 Seconds | R2: Same as R1, but use a small amount of violet dye | R3: Bleaching with $NaClO_2$ optical whitening HT-process |
|---|---|---|---|---|
| $PET/K_3Al(C_2O_4)_3$ | 5 | 31.8% | 25.7% | 6.4% |
| $PET/K_3Al(C_2O_4)_3$ | 10 | 24.2% | 19.7% | 2.5% |
| PET without* $K_3Al(C_2O_4)_3$ | 5 | 54.2% | 49.8% | 20.0% |
| PET without* $K_3Al(C_2O_4)_3$ | 10 | 47.2% | 45.3% | 16.0% |

*DIOLEN 12® polyester (Enka A.G., Wuppertal, Germany), 1.7 dtex
**Rc = Reflected Light When Surface is Clean
Rd = Reflected Light When Surface is Dirty, After Treatment of a Mixture of 30 parts $H_2O$ and 500 ppm Carbon Black, to 1 Part Textile It is recommended that MILEASE T®(ICI Imperial Chemical Industries, London, England) be employed as a finisher in the finishing stages prior to singeing; in the alternative, ZELCON 4951® (E. I. Dupont de Nemours, Wilmington, Del.) or MIGAFAR® (Ciba-Geigy, Basel, Switzerland) finishers may be employed at the same stage. It is recommended that after textile spinning, the yarn should be bathed in a solution of SOLVITOSE WS 60® lubricant (BASF, Ludswighafen, Germany) in a concentration of 200 g/l in order to reduce friction and yarn breaks in weaving.

Comparative testing showed that $PET/K_3Al(C_2O_4)_3$ yarn having only 2% moisture regain was a noticeable advance in the art because of its roughness of the surface of the filaments. $PET/K_3Al(C_2O_4)_3$ yarn is thought to have its best applications for light-colored fabrics, including shirts, underwear, light-colored socks, towels and sheets. Fabrics made entirely of $PET/K_3Al(C_2O_4)_3$ yarn have a dull appearance, making them excellent for the manufacture of dress shirts and knit sportswear.

EXAMPLE 18

Table 17 summarizes moisture regain tests of various yarns comprising various polymers and copolymers, and different simple and complex oxalato complexes with and without hydrofixation:

TABLE 17

| Polyester Mass | Hydroset? | Oxalato Salt Formula | Oxalato Salt Proportion (Referred To On Polyester Mass) | Moisture Uptake 40° C./92% R.H. |
|---|---|---|---|---|
| Polyethylene terephthalate (PET) | No | Mg-Oxalate | 10% | 1.6 |
| PET | Yes | Mg-Oxalate | 10% | 0.6 |
| PET | No | Na₃[Al(C₂O₄)₃] | 10% | 5.8 |
| PET | Yes | Na₃[Al(C₂O₄)₃] | 10% | 6.0 |
| PET | No | KBa[Al(C₂O₄)₃] | 10% | 0.6 |
| PET | Yes | KBa[Al(C₂O₄)₃] | 10% | 0.5 |
| PET | No | K₂[Zn(C₂O₄)₂] | 10% | 3.2 |
| PET | Yes | K₂[Zn(C₂O₄)₂] | 10% | 3.0 |
| PET | No | K₄[Zr(C₂O₄)₄] | 10% | 3.6 |
| PET | Yes | K₄[Zr(C₂O₄)₄] | 10% | 4.1 |
| PET | No | K₂[Mg(C₂O₄)₂] | 10% | 1.9 |
| PET | Yes | K₂[Mg(C₂O₄)₂] | 10% | 2.6 |
| PET | No | K₃Al(C₂O₄)₃ | 10% | 4.3 |
| Copolymer of PET having K₃Al(C₂O₄)₃ with 8 mol % Adipic Acid | | | | |

| Polyester Mass | Hydrofixed? | Oxalato Salt Formula | Oxalato Salt Proportion (Referred to On Polyester Mass) | Density g/cm³ | Moisture Uptake 40° C./ 92% R.H. | Overall K₃Al(C₂O₄)₃ Content % Al | % K | % K₃Al(C₂O₄)₃ | Pore <150A | Volume <7500A | cm³/g <20,000A |
|---|---|---|---|---|---|---|---|---|---|---|---|
| Copolymer of PET having K₃Al(C₂O₄)₃ with 8 mol % Adipic Acid | Yes | K₃Al(C₂O₄)₃ | 10% | | 7.9 | | | | | | |
| Copolymer of PET without K₃Al(C₂O₄)₃ with 8 mol % Adipic Acid | No | — | — | | 0.2 | | | | | | |
| Copolymer of PET without K₃Al(C₂O₄)₃ with 8 mol % Azelaic Acid | Yes | — | — | | 0.1 | | | | | | |
| BIKO-Skin:PET, core:PET/K₃Al(C₂O₄)₃ | No | K₃Al(C₂O₄)₃ | Core - 10% Skin - None | 1.313 | 4.2 | 0.49 | 1.88 | 7.0 | 0.036 | 0.046 | 0.059 |
| BIKO-Skin:PET, core:PET/K₃Al(C₂O₄)₃ | Yes | K₃Al(C₂O₄)₃ | Core - 10% Skin - None | 1.181 | 7.2 | 0.49 | 1.91 | 7.2 | 0.104 | 0.133 | 0.139 |
| PBT (from DMT, Butandiol) | No | K₃Al(C₂O₄)₃ | 10% | 1.285 | 8.1 | 0.78 | 3.08 | 11.4 | 0.038 | 0.057 | 0.062 |
| PBT | Yes | K₃Al(C₂O₄)₃ | 10% | 1.117 | 6.2 | 0.42 | 1.50 | 5.6 | 0.082 | 0.197 | 0.207 |
| PET | No | Na Oxalate | 10% | | 0.5 | | | | | | |

| Polyester Mass | Hydrofixed? | Oxalato Salt Formula | Oxalato Salt Proportion (Referred to On Polyester Mass) | 40° C./92% R.H. |
|---|---|---|---|---|
| PET | Yes | Na Oxalate | 10% | 0.5 |
| Copolymer of PET + 4 mol % Isoph- | No | K₃Al(C₂O₄)₃ | 10% | 7.4 |

TABLE 17-continued

| | | | |
|---|---|---|---|
| thalic Acid Dimethyl Ester | | | |
| Copolymer of PET + 4 mol % Isophthalic Acid Dimethyl Ester | Yes | K₃Al(C₂O₄)₃ | 10% | 8.2 |
| Copolymer of PET + 8 mol % Azelaic Acid | No | K₃Al(C₂O₄)₃ | 10% | 6.7 |
| Copolymer of PET + 8 mol % Azelaic Acid | Yes | K₃Al(C₂O₄)₃ | 10% | 8.9 |

We claim:

1. A hydroset hydrophilic polyester fiber characterized by a pore system, comprising:
   a suitable polyester containing active portions of a suitable oxalato complex sufficient to effect a moisture regain of at least about 2% by weight measured at 40° C. and relative humidity of 92%, having a pore system capable of capillary condensation at 20° C. and a relative humidity of less than 97% in said polyester, said active portions of oxalato complex having been incorporated into said polyester and then hydroset.

2. The fiber of claim 1, wherein the pore system has both micropores and macropores.

3. The fiber of claim 1, having an apparent density of less than 1350 kg/m$^3$.

4. The fiber of claims 1 or 2 having an apparent density of from about 1050 to about 1150 kg/m$^3$.

5. The fiber of claim 1 having a moisture regain of about 5 to about 5 wt. % at 40° C. and 92% relative humidity.

6. The fiber of claims 1 or 5 having micropore radii of less than 30 nm.

7. The fiber of claim 1 having micropore radii of from about 5 to about 15 nm.

8. The fiber of claims 1 or 7 having micropores whose total volume exceeds 0.04 cm$^3$/g.

9. The fiber of claim 1 or 6 having micropores which have radii ranging from about 5 nm to about 15 nm and a volume from about 0.04 cm$^3$/g to about 0.15 cm$^3$/g.

10. The fiber of claim 1, having nonspherical micropores, with a major portion of said pores being oriented parallel to the fiber axis.

11. The fiber of claim 1 having a water retention capacity in excess of 10%.

12. The fiber of claim 11 having a water retention capacity ranging between 20 and 30%.

13. The fiber of claims 1 or 11, comprising polyesters or copolyesters of terephthalic acid.

14. The fiber of claim 1, wherein said oxalato complex is the formula:
   $M_n [Z(C_2O_4)_m]$, wherein:
   M = at least one of the ions Li, Na, K, Rb, or Cs;
   Z = one or more complex-forming central atoms selected from the group consisting of Mg, Ca, Sr, Ba, Zr, Hf, Ce, V, Cr, Mn, Fe, Co, Ni, Cu, Zn, Cd, B, Al, Ga, In, Sn, Pb, and Sb;
   $n \approx 1$, $\approx 2$, $\approx 3$ or $\approx 4$; and
   $m \approx 2$, $\approx 3$, $\approx 4$.

15. The fiber of claim 1, wherein the oxalato complex is $K_3Al(C_2O_4)_3$.

16. The fiber of claim 1, wherein the oxalato complex is $K_3Al(C_2O_4)_3$ and the suitable polymer comprises a polyester or copolyester of polybutylene or polyethylene terephthalate.

17. The fiber of claim 1, having a bicomponent core-skin structure wherein the core and the skin of the fiber contain different polyesters.

18. The fiber of claim 17, wherein the skin of the bicomponent fiber consists of an unmodified polyester and the core consists of an oxalato-complex-containing polyester.

* * * * *